US009963506B2

(12) United States Patent
Chen et al.

(10) Patent No.: US 9,963,506 B2
(45) Date of Patent: May 8, 2018

(54) HUMAN-MOUSE CHIMERIC ANTI-CD147 ANTIBODY WITH NON-FUCOSYLATED GLYCOSYLATION

(71) Applicant: Fourth Military Medical University, Xi'an (CN)

(72) Inventors: Zhinan Chen, Xi'an (CN); Zheng Zhang, Xi'an (CN); Yang Zhang, Xi'an (CN); Fei Feng, Xi'an (CN); Muren Huhe, Xi'an (CN); Xiangmin Yang, Xi'an (CN)

(73) Assignee: FOURTH MILITARY MEDICAL UNIVERSITY, Xi'an (CN)

( * ) Notice: Subject to any disclaimer, the term of this patent is extended or adjusted under 35 U.S.C. 154(b) by 0 days. days.

(21) Appl. No.: 14/877,080

(22) Filed: Oct. 7, 2015

(65) Prior Publication Data
US 2017/0101469 A1 Apr. 13, 2017

(51) Int. Cl.
*A61K 31/337* (2006.01)
*C07K 16/28* (2006.01)
*A61K 45/06* (2006.01)
*A61K 31/475* (2006.01)
*A61K 31/7068* (2006.01)
*A61K 33/24* (2006.01)
*A61K 39/00* (2006.01)

(52) U.S. Cl.
CPC ........ *C07K 16/2803* (2013.01); *A61K 31/337* (2013.01); *A61K 31/475* (2013.01); *A61K 31/7068* (2013.01); *A61K 33/24* (2013.01); *A61K 45/06* (2013.01); *C07K 16/2863* (2013.01); *A61K 2039/505* (2013.01); *C07K 2317/24* (2013.01); *C07K 2317/41* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS 6,602,684 B1 * 8/2003 Umana ................. C07K 16/00
435/320.1

FOREIGN PATENT DOCUMENTS

CN 1186445 C 1/2005
CN 104086654 A 10/2014
WO WO/2006/029459 * 3/2006

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Yu et al. (Landes Bioscience, mAbs 4:4, 475-487 Jul./Aug. 2012).*
Miyako Baba et al. "Blocking CD147 induces cell death in cancer cells through impairment of glycolytic energy metabolism", Biochemical and Biophysical Research Communications 374 (2008) 111-116, Published Online First Jul. 9, 2008; DOI: 10.1016/j.bbrc.2008.06.122.
Huijie Bian et al. "Randomized Trial of [131I] Metuximab in Treatment of Hepatocellular Carcinoma After Percutaneous Radiofrequency Ablation", Oxford University Press, Published Online First Sep. 10, 2014; DOI:10.1093/jnci/dju239.
Hongmin Chen et al. "Co-expression of CD147EMMPRIN with monocarboxylate transporters and multiple drug resistance proteins is associated with epithelial ovarian cancer progression", Clin Exp Metastasis (2010) 27:557-569, Published Online First Jul. 24, 2010; DOI:10.1007/s10585-010-9345-9.
Zhi-Nan Chen et al. "Targeting radioimmunotherapy of hepatocellular carcinoma with iodine (131I) metuximab injection: Clinical Phase I/II trials", Int. J. Radiation Oncology Biol. Phys., Published Online First Dec. 13, 2005; DOI:10.1016/j.ijrobp.2005.12.034; vol. 65, No. 2, pp. 435-444, 2006.
Royston Jefferis "Recombinant antibody therapeutics the impact of glycosylation on mechanisms of action", Trends in Pharmacological Sciences vol. 30 No. 7, Published Online First Jun. 22, 2009; DOI:10.1016/j.tips.2009.04.007.
Hiroaki Kataoka et al. "Tumor cell-derived collagenase-stimulatory factor increases expression of interstitial collagenase, stromelysin, and 72-kDa gelatinase.ancer Res-1993-Kataoka-3154-8", Cancer Research 53. 3154-3158. Jul. 1, 1993.
P. Kirk et al. "CD147 is tightly associated with lactate transporters MCT1 and MCT4 and facilitates their cell surface expression", The EMBO Journal, vol. 19 No. 15 pp. 3896-3904, 2000.
Yu Li et al. "HAb18G (CD147), a cancer-associated biomarker and its role in cancer detection", Histopathology 2009, 54, 677-687. DOI: 10.1111/j.1365-2559.2009.03280.x.

(Continued)

Primary Examiner — Laura B Goddard
Assistant Examiner — Meera Natarajan
(74) Attorney, Agent, or Firm — Jun He Law Offices P.C.; Zhaohui Wang

(57) ABSTRACT

The present disclosure relates to a nucleotide sequence comprising the sequence of SEQ ID NO: 5, and/or sequence of SEQ ID NO: 6, vector and host cell line comprising the nucleotide. The present disclosure also relates to an antibody that binds to extracellular region of human CD147, wherein the antibody comprises a heavy chain variable region having the amino acid sequence of SEQ ID NO: 2, and/or a light chain variable region having the amino acid sequence of SEQ ID NO: 1, and the antibody contains a glycoform lacking both fucose residues and xylose residues, pharmaceutical composition comprising the antibody or fragment thereof, the method of producing the antibody or fragment thereof, and use of the pharmaceutical composition in treatment of CD147 expression-related diseases.

22 Claims, 8 Drawing Sheets

(56) References Cited

OTHER PUBLICATIONS

Qiang Liang et al. "HAb18GCD147 Regulates Vinculin-Mediated Focal Adhesion and Cytoskeleton Organization in Cultured Human Hepatocellular Carcinoma Cells", PLOS ONE, vol. 9 | Issue 7 | e102496, Published Online First Jul. 17, 2014.

Mahmoud Orazizadeh et al. "CD147 (Extracellular Matrix Metalloproteinase Inducer-EMMPRIN) Expression by Human Articular Chondrocytes", Iranian Biomedical Journal 12 (3): 153-158 (Jul. 2008).

Nancy J. Philp et al. "Loss of MCT1 MCT3 and MCT4 Expression in the Retinal Pigment Epithelium and Neural Retina of the 5A11 Basigin Null Mouse", Invest Ophthalmol Vis Sci. 2003;44:1305-1311; DOI:10.1167/ iovs.02-0552.

W Schneiderhan et al. "CD147 silencing inhibits lactate transport and reduces malignant potential of pancreatic cancer cells in in vivo and in vitro models", Gut 2009;58:1391-1398;DOI:10.1136/gut.2009.181412; Published Online First Jun. 7, 2009.

Jing Xu et al. "A randomized controlled trial of licartin for preventing hepatoma recurrence after liver transplantation", Wiley InterScience; DOI:10.1002/hep.21465.

Jing Xu et al. "HAb18GCD147 functions in invasion and metastasis of hepatocellular carcinoma", Mol Cancer Res 2007;5(6). Jun. 2007.

H. Z. Zeng et al. "Expression of CD147 in advanced non-small cell lung cancer correlated with cisplatin-based chemotherapy resistance", Neoplasma 58, 5, 2011; DOI: 10.4149/neo_2011_05_449.

Shuang Zhao et al. "CD147 promotes MTX resistance by immune cells through up-regulating ABCG2 expression and function", Journal of Dermatological Science 70 (2013) 182-189; DOI: 10.1016/j.jdermsci2013.02.005.

Wei Zou et al. "inhibition of CD147 gene expression via RNA interference reduces tumor cell invasion, tumorigenicity and increases chemosensitivity to paclitaxel iin HO-8910pm cells", Cancer Letters 248 (2007) 211-218; DOI: 10.1016/i.canlet.2006.07.005.

Zheng Zhang et al. "Preclinical Pharmacokinetics, Tolerability, and Pharmacodynamics ofMetuzumab, a Novel CD147 Human-Mouse Chimeric and Glycoengineered Antibody", Published OnlineFirst Nov. 5, 2014; DOI: 10.1158/1535-7163.MCT-14-0104.

\* cited by examiner

HUMAN-MOUSE CHIMERIC ANTI-CD147 ANTIBODY WITH NON-FUCOSYLATED GLYCOSYLATION

FIELD OF THE INVENTION

The present disclosure relates to a human-mouse chimeric anti-CD147 antibody with specific glycosylation profile in Fc region.

BACKGROUND OF THE INVENTION

CD147 is a highly glycosylated transmembrane protein that belongs to the immunoglobulin superfamily. CD147 is commonly over-expressed in many tumors (Li et al., 2009. HAb18G (CD147), a cancer-associated biomarker and its role in cancer detection. Histopathology 54, 677-687.), including carcinomas of liver, lung, breast, pancreas, prostate, and bladder. CD147 over expression level is correlated with tumor histopathologic type and clinical stage of disease. Importantly, CD147 surface expression is closely associated with tumorigenesis, tumor progression and reduced patient survival in various cancers, and these facts validate CD147 as a therapeutic target for cancer treatment.

Antibody Dependent Cell-mediated Cytotoxicity (ADCC) is a major clinical mechanism of action for therapeutic antibodies. Generally, when the antibody binds to a tumor target on the surface of a cell in a tumor tissue of a cancer patient, the Fc region of the antibody attracts effector cells, such as NK cells, by binding to the surface Fc receptor (e.g. CD16) of the NK cells. Binding of the Fc region to CD16 of the effector cells induces secretion of perforin and granzyme that lead to apoptosis of the target cells. Macrophages, neutrophils and eosinophils can also be activated by the Fc effector function.

ADCC efficacy of IgG antibodies is significantly dependent on Fc glycosylation patterns (Jefferis, 2009). We previously generated an anti-CD147 murine monoclonal antibody, HAb18 (U.S. Pat. No. 7,638,619, PCT/CN03/00188 and China patent No. ZL02114471.0), and developed a 131I-labeled HAb18 F(ab')$_2$ (named Licartin) to treat liver cancer (Xu et al., 2007a; A randomized controlled trial of Licartin for preventing hepatoma recurrence after liver transplantation. Hepatology 45, 269-276). Licartin has been shown to be effective in the treatment of liver cancer, demonstrating anti-CD147 antibodies as molecular targeted therapeutics. Although efficient, safe and tolerated in therapy, Licartin suffered from immunogenicity which triggers generation of human-anti-mouse antibodies (HAMA) in 4 out of 130 treated patients without affecting therapeutic results (Chen et al., 2006; Targeting radioimmunotherapy of hepatocellular carcinoma with iodine (131I) metuximab injection: clinical phase I/II trials. International journal of radiation oncology, biology, physics 65, 435-444.). Such limitations have prompted efforts to improve the efficacy and tolerability of HAb18 through antibody engineering, as well as the inconvenience of administration of a non-radioactively labelled therapeutic antibody. The present disclosure addresses these and other needs and provides several additional benefits for efficient and safe treatment of cancer patients, which will be described in the remainder of this document.

BRIEF SUMMARY OF THE INVENTION

In one aspect, the present disclosure provides nucleotide sequences comprising the sequence of SEQ ID NO: 5, and/or sequence of SEQ ID NO: 6. In one aspect, the present disclosure provides nucleotide sequences comprising the sequence of SEQ ID NO: 7, and/or sequence of SEQ ID NO: 8.

In another aspect, the present disclosure provides vectors comprising the nucleotide sequence comprising the sequence of SEQ ID NO: 5, and/or sequence of SEQ ID NO: 6. In another aspect, the present disclosure provides vectors comprising the nucleotide sequence comprising the sequence of SEQ ID NO: 7, and/or sequence of SEQ ID NO: 8.

In another aspect, the present disclosure provides host cells comprising a vector, wherein the vector comprises the nucleotide sequence comprising the sequence of SEQ ID NO: 5, and/or sequence of SEQ ID NO: 6. In another aspect, the present disclosure provides host cells comprising a vector, wherein the vector comprises the nucleotide sequence comprising the sequence of SEQ ID NO: 7, and/or sequence of SEQ ID NO: 8.

In another aspect, the present disclosure provides antibodies that bind to an extracellular region of human CD147, wherein the antibodies comprise a heavy chain variable region having the amino acid sequence of SEQ ID NO: 2, and the antibodies contain a glycoform lacking both fucose residues and xylose residues. In some embodiments, the antibodies further comprise a light chain variable region having the amino acid sequence of SEQ ID NO: 1. In some embodiments, the antibodies comprise a light chain having the amino acid sequence of SEQ ID NO: 3. In some embodiments, the antibodies comprise a heavy chain having the amino acid sequence of SEQ ID NO: 4.

In some embodiments, the antibodies or fragments thereof comprises a predominant portion of glycoforms comprising N-linked oligosaccharides comprising five mannose residues (also called Mannose-5). In some embodiments, the antibodies or fragments thereof comprise solely a glycoform comprising N-linked Mannose-5. In some embodiments, the antibody has a glycosylation profile as analyzed by High-Performance Anion Exchange Chromatography with Pulsed Amperometric Detection (HPAEC-PAD) that is substantially equivalent to that of Metuzumab as shown in FIG. 6.

In some embodiments, the antibodies are obtained from an acetyl-glucosamine transferase deficient cell line. In some embodiments, the cell line is CHO cell line.

In some embodiments, the ADCC activity of the antibodies containing a glycoform that lacks both fucose residues and xylose residues is at least 2 times, 5 times, 10 times or 20 times higher than the ADCC activity of an antibody that has a glycoform comprising fucose residues, xylose residues or both.

In another aspect, the present disclosure provides pharmaceutical compositions comprising an antibody that binds to an extracellular region of human CD147, or a fragment of such antibody, and a pharmaceutically acceptable vehicle or excipient, wherein the antibody comprises a heavy chain variable region having the amino acid sequence of SEQ ID NO: 2 and a light chain variable region having the amino acid sequence of SEQ ID NO: 1, and the antibody contains a glycoform lacking both fucose residues and xylose residues. In some embodiments, the antibodies comprise a light chain having the amino acid sequence of SEQ ID NO: 3. In some embodiments, the antibodies comprise a heavy chain having the amino acid sequence of SEQ ID NO: 4. In some embodiments, the pharmaceutical compositions further comprise a chemotherapeutic agent. In some embodiment, the chemotherapeutic agent is selected from gemcitabine, cisplatin, paclitaxel, and navelbine.

In another aspect, the present disclosure provides methods for producing an antibody that binds to an extracellular region of human CD147, or a fragment of such antibody, comprising: obtaining a nucleotide sequence encoding for a heavy chain variable region having the amino acid sequence of SEQ ID NO: 2 and nucleotide sequence encoding for a light chain variable region having the amino acid sequence of SEQ ID NO: 1; constructing an vector comprising the nucleotide sequence or fragment of the nucleotide sequence; transfecting the vector into an acetyl-glucosamine transferase deficient cell line; culturing the transfected cell line in media; and obtaining the antibody or the fragment of the antibody from the culture.

In another aspect, the present disclosure provides methods for producing an antibody that binds to an extracellular region of human CD147, or fragment thereof, comprising: culturing a host cell comprising a vector comprising a first nucleotide sequence encoding for a heavy chain variable region having the amino acid sequence of SEQ ID NO: 2 and a second nucleotide sequence encoding for a light chain variable region having the amino acid sequence of SEQ ID NO: 1 under a condition to allow expression of the antibody or fragment thereof comprising the heavy chain and the light chain; and obtaining the antibody or the fragment thereof from the culture.

In some embodiments, the step of culturing the transfected cell line in media comprises culturing the transfected cell line at 36-38° C. for a first period and then at 30-32° C. for a second period. In some embodiments, the first period is 4-10 days. In some embodiments, the second period is 11-21 days.

In some embodiments, the expression level of the antibody by the cell line is at least 100 mg/L, at least 200 mg/L, or at least 300 mg/L. In some embodiments, the percentage of non-glycosylated heavy chain calculated based on the total amount of antibody obtained is less than 10%, 7%, 5% or 3%. In some embodiments, the cell line is an acetyl-glucosamine transferase deficient CHO cell line.

In another aspect, the present disclosure provides methods for treating a disease associated with human CD147 in a subject in need thereof, comprising administering an effective amount of an antibody that binds to an extracellular region of human CD147, or fragment thereof, wherein the antibody comprises a heavy chain variable region having the amino acid sequence of SEQ ID NO: 2 and a light chain variable region having the amino acid sequence of SEQ ID NO: 1, and the antibody contains a glycoform lacking both fucose residues and xylose residues. In some embodiments, the antibody comprises a light chain having the amino acid sequence of SEQ ID NO: 3. In some embodiments, the antibody comprises a heavy chain having the amino acid sequence of SEQ ID NO: 4. In some embodiments, the methods further comprise administering a chemotherapeutic agent to the subject. In some embodiments, the chemotherapeutic agent is selected from gemcitabine, cisplatin, paclitaxel, and navelbine. In some embodiments, the disease is cancer. In some embodiments, the cancer is lung cancer, liver cancer, esophagus cancer, ovarian cancer, stomach cancer, breast cancer, cervical cancer, or colon cancer. In some embodiments, the disease is lung cancer. In some embodiments, the disease is non-small cell lung cancer.

DETAILED DESCRIPTION OF THE INVENTION

Figure 1:
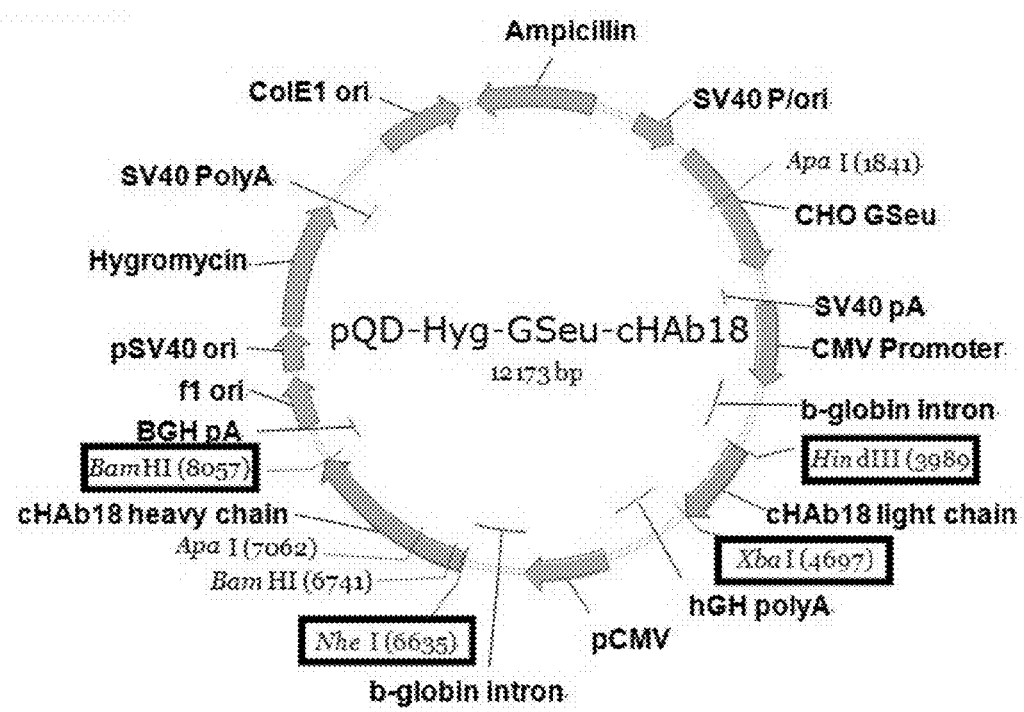
FIG. 1 shows the construction diagram of the pQD-Hyg-GSeu-cHAb18 expression vector.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Nucleotide Sequence

In one aspect, the present disclosure provides nucleotide sequences encoding an antibody or a fragment thereof, comprising the sequence of SEQ ID NO: 5 or a degenerate variant thereof, and/or sequence of SEQ ID NO: 6 or a degenerate variant thereof.

In some embodiments, the nucleotide sequence comprises the sequence of SEQ ID NO: 5. In some embodiments, the nucleotide sequence comprises the sequence of SEQ ID NO: 6. In some embodiments, the nucleotide sequence comprises both the sequence of SEQ ID NO: 5 and the sequence of SEQ ID NO: 6.

In some embodiments, the nucleotide sequence comprises the sequence of SEQ ID NO: 7. In some embodiments, the nucleotide sequence comprises the sequence of SEQ ID NO: 8. In some embodiments, the nucleotide sequence comprises both the sequence of SEQ ID NO: 7 and the sequence of SEQ ID NO: 8.

The term "degenerate variant" as used herein refers to a nucleic acid molecule which includes one or more alternative genetic codons to those present in the parent sequence, yet encodes the same amino acid sequence due to the degeneracy of the genetic codons.

Without wishing to be bound by theory, but it is believed that SEQ ID NO: 5 and SEQ ID NO: 6 are particularly advantageous in expression in certain types of host cells such as CHO cells, partly because of the optimization in the genetic codon usage based on the host cells or other types of cells.

The nucleotide sequence used in the present disclosure can be prepared by any methods known in the art, including but not limited to, chemical synthesis, molecular cloning and etc. (see, e.g. for details, Sambrook, Fritsch & Maniatis, Molecular Cloning: A laboratory Manual, 2nd Edition, Cold Spring Harbor Laboratory, 1989).

The term "antibody" as used herein includes any immunoglobulin, monoclonal antibody, polyclonal antibody, multispecific antibody, and bispecific (bivalent) antibody that binds to a specific antigen. A native intact antibody comprises two heavy chains and two light chains. Each heavy chain consists of a variable region ($V_H$) and a first, second, and third constant region ($C_{H1}$, $C_{H2}$, $C_{H3}$), while each light chain consists of a variable region ($V_L$) and a constant region ($C_L$). The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The Fc portion of an antibody refers to that portion of the antibody consisting of the second and third constant regions of a first heavy chain bound to the second and third constant regions of a second heavy chain via disulfide bonding. The Fc portion of the antibody is responsible for various effector functions such as ADCC, and Complement Dependent Cytotoxicity (CDC), but does not function in antigen binding.

A "fragment" of an antibody as used herein refers to an antigen-binding portion or full length of a heavy chain or a light chain of an antibody, or an antigen-binding portion of both the heavy chain and the light chain of an antibody.

Vector

In another aspect, the nucleotide sequence described above may be inserted into one or more vectors. The term "vector" as used herein, refers to a polynucleotide vehicle capable of transforming or transfecting cells and allowing gene expression in the cells. A vector can be an expression vector and a cloning vector. The present disclosure provides vectors (e.g. expression vectors) containing the nucleotide sequence provided herein encoding the antibody or a fragment thereof, at least one promoter operably linked to the nucleotide sequence, and at least one selection marker. The expression vectors of the present disclosure can be viral vectors, plasmids, phages and cosmids. Examples include, such as, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid PCR 2.1, pCMV, pEGFP, pIRES, pQD-Hyg-GSeu, and etc.

In some embodiments, the present disclosure provides vectors capable of expressing the antibody provided herein or a fragment thereof, comprising the nucleotide sequence having the sequence of SEQ ID NO: 5, and/or sequence of SEQ ID NO: 6.

In some embodiments, the vectors comprise the nucleotide sequence comprising the sequence of SEQ ID NO: 5. In some embodiments, the vectors comprise the nucleotide sequence comprising the sequence of SEQ ID NO: 6. In some embodiments, the vectors comprise the nucleotide sequence comprising both the sequence of SEQ ID NO: 5 and the sequence of SEQ ID NO: 6. In some embodiments, the vectors comprise the nucleotide sequence having the sequence of SEQ ID NO: 7, and/or sequence of SEQ ID NO: 8.

Host Cell

In another aspect, the present disclosure provides host cells comprising a vector provided herein, wherein the vector comprises the nucleotide sequence having the sequence of SEQ ID NO: 5, and/or sequence of SEQ ID NO: 6. In some embodiments, the host cells comprise a vector provided comprising the nucleotide sequence having the sequence of SEQ ID NO: 7, and/or sequence of SEQ ID NO: 8.

In some embodiments, the host cells comprise a vector provided herein, wherein the vector comprises the nucleotide sequence having the sequence of SEQ ID NO: 5. In some embodiments, the host cells comprise a vector provided herein, wherein the vector comprises the nucleotide sequence having the sequence of SEQ ID NO: 6. In some embodiments, the host cells comprise a vector provided herein, wherein the vector comprises the nucleotide sequence having both the sequence of SEQ ID NO: 5 and the sequence of SEQ ID NO: 6.

In some embodiments, the nucleotide sequence included in the vector contains genetic codons which are selected for accommodating host cell codon usage bias. The term "codon usage bias" as used herein, refers to the extent to which one codon is preferentially used by the host cell to code for a particular amino acid over all other possible codons for the same amino acid. Codon usage bias is due to the differences in the codon usage in the genome of different species. The genetic codons contained in the vector can be accommodated based on the host cell or other types of cells.

The term "host cell" as used herein refers to a cell into which an exogenous polynucleotide and/or a vector has been introduced. A host cell can be transfected with a vector of the present disclosure. Host cells may be eukaryotic cells that are capable of producing antibody with glycosylation. Examples of eukaryotic cells include animal cells such as mammalian cells. For example, the host cell may be cell lines, such as but are not limited to HeLa, HEK-293, NIH3T3, COS, Chinese Hamster Ovary (CHO) cells, NS0, PER.C6, K562, L1.2, JY, BHK, K562, 293F, 3T3, and Jurkat. The CHO cells may include, but not be limited to, CHO/DHFR⁻ (dihyrofolate reductase deficiency) or CHO/GS⁻ (glutamine synthetase deficientcy) cells. Examples of CHO cells include those described in documents such as Journal of Experimental Medicine, 108, 945 (1958); Proc. Natl. Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Natl. Acad. Sci. USA, 77, 4216 (1980); Proc. Natl. Acad. Sci., 60, 1275 (1968); Cell, 6, 121 (1975); Molecular Cell Genetics, Appendix I, II (pp. 883-900); and the like. In addition, CHO-K1 (ATCC CCL-61), DUXB11 (ATCC CCL-9096), CHO DG44 and Pro-5 (ATCC CCL-1781) registered in ATCC (The American Type Culture Collection) and a commercially available CHO-S (Life Technologies, Cat #11619) or sub-cell lines obtained by adapting the cell lines using various media can also be exemplified. In some embodiments, the CHO cells are adapted to suspension cell culture. In some embodiments, the CHO cells are adapted to serum free culture.

In some embodiments, the CHO cells are modified to provide for a variant glycosylation pattern as compared to an unmodified parental host cell. For example, the CHO cells can be modified to over-express or under-express or knock-out one or more enzymes responsible for glycosylation. In some embodiments, the CHO cells are acetyl-glucosamine transferase deficient.

Antibody

The present disclosure provides antibodies that bind to an extracellular region of human CD147, wherein the antibody comprises a heavy chain having the amino acid sequence of SEQ ID NO: 4, and the antibody contains a glycoform lacking fucose residues, xylose residues, or both. In some embodiments, the antibodies further comprise a light chain having the amino acid sequence of SEQ ID NO: 3.

In some embodiments, the antibody is a human-mouse chimeric antibody. A "human-mouse chimeric antibody" refers to an antibody in which the heavy/light chain variable regions are derived from mouse, and the heavy/light chain constant regions are derived from human. In some embodiments, the human-mouse chimeric antibodies comprise a constant region derived from human antibody IgG1, IgG2, or IgG4. In some embodiments, the antibody comprises a constant region of human antibody IgG1.

In some embodiments, the antibodies provided herein are recombinant antibodies and fragments thereof that recognize an extracellular region of CD147 and have cytotoxicity on CD147 expressing cells. Exemplary antibodies of the present disclosure include, HAb18, cHAb18, and variants thereof having certain glycoforms.

The HAb18 antibody is a monoclonal murine antibody produced by a hybridoma cell line generated using a BALB/c mice immunized with a cell suspension extracted from fresh human HCC tissues. The hybridoma cell line has been deposited under the deposit number of CGMCC NO. 0426 with China General Microbiological Culture Collection Center having the address of NO. 1 West Beichen Road, Chaoyang District, Beijing 100101, P. R. China.

The cHAb18 antibody is a human-mouse chimeric anti-CD147 antibody which comprises a heavy chain variable domain and a light chain variable domain derived from HAb18, and constant domains derived from a human antibody IgG1. The cHAb18 comprises a heavy chain amino acid sequence of SEQ ID NO: 4, and light chain amino acid sequence of SEQ ID NO: 3, in which the heavy chain variable domain has an amino acid sequence of SEQ ID NO: 2, and light chain variable domain has an amino acid sequence of SEQ ID NO: 1.

In some embodiments, the antibodies and fragments thereof comprise a particular glycoform. As used herein, the term "glycoform" with respect to an antibody or fragment thereof, refers to a particular glycosylated form of the antibody or fragment thereof. When there is at least one amino acid residue in the antibody or fragment thereof that has the potential to be glycosylated (i.e., to be linked to a glycan or different glycans or different sets of glycans), each different version of the antibody or antibody fragment linked to a particular glycan or glycans is referred to as a glycoform. In other words, different glycoforms share the same amino acid sequence but have different glycans or oligosaccharides attached to the glycosylation site(s). Glycosylated antibodies and fragments thereof can be recombinantly produced in host cells where the cellular glycosylation machinery transfers one or more glycans to the amino acid sequence of the antibodies and fragments thereof, thereby producing a population of glycosylated antibodies containing certain glycoforms.

In some embodiments, the antibodies and fragments thereof provided herein are glycosylated in the Fc region. In some embodiments, the antibodies and fragments thereof provided herein carry N-linked oligosaccharides in its Fc region. For example, the antibodies and fragments thereof can carry two N-linked oligosaccharides in its Fc region, one on each heavy chain.

In some embodiments, the antibodies and fragment thereof provided herein contain a glycoform which specifically lacks fucose residues, xylose residues, or both. In some embodiments, the antibodies and fragment thereof provided herein consist of one or more glycoforms which specifically lack(s) fucose residues, xylose residues, or both. The term "lack" or "lacking" with respect to certain monosaccharide residues as used herein is intended to mean such monosaccharide residues are absent or are at a level that is too low to be detected using a detection method known in the art, for example, High-Performance Anion Exchange Chromatography with Pulsed Amperometric Detection (HPAEC-PAD). Other detection methods may also be used to detect the oligosaccharides, for example, Matrix-Assisted Laser Desorption/Ionization Time of Flight Mass Spectrometry (MALDI/TOF-MS).

In some embodiments, the ADCC activity of the antibodies that contain a glycoform lacking both fucose residues and xylose residues are at least 2 times, 5 times, 10 times, 20 times, 40 times, 60 times, or 100 times higher than the ADCC activity of an antibody that contains a glycoform comprising fucose residues, xylose residues, or both.

ADCC is a cell-mediated reaction in which antigen-nonspecific cytotoxic cells that express Fc Receptors (FcRs) (e.g., natural killer (NK) cells, neutrophils, and macrophages which are included in PBMC or spleen) recognize antibody bound to the surface of a target cell and subsequently cause lysis of (i.e., "kill") the target cell. The term "ADCC activity" refers to the ability of an antibody or Fc fusion protein to elicit an ADCC reaction. ADCC activity can be assessed directly using an in vitro assay, e.g., a $^{51}$Cr release assay using peripheral blood mononuclear cells (PBMC) and/or spleen effector cells as described in the Examples and Shields et al. (2001) J. Biol. Chem., 276:6591-6604, or any other suitable method. ADCC activity may be expressed as a concentration of antibody at which the lysis of target cells is half-maximal. The ADCC activity of an antibody generally depends on the binding affinity of the antibody to target cell, which could be affected by the glycoform of N-linked oligosaccharide of the antibody.

In some embodiments, the antibodies and fragment thereof provided herein contain a glycoform comprising Mannose-5 glycans. In some embodiments, the antibodies and fragments thereof provided herein contain N-linked Mannose-5 glycans. The term "Mannose-5" as used herein refers to a chain of five mannose residues which are added sequentially to the core monosaccharide(s). Core monosaccharide(s) are the monosaccharide(s) which are synthesized at the initial stage of glycosylation and form the starting point for addition of more monosaccharides. For example, in certain glycosylation process, two N-acetylglucosamine (GlcNAc) monosaccharides form the core monosaccharides upon which the additional sugar residues, for example, mannose residues are further added. Mannose-5 can be a linear sugar chain or a branched sugar chain. In some embodiments, Mannose-5 is a two-armed branched structure in which one arm consists of one mannose residue and the other arm consists of three mannose residues, with a joint mannose residue which links both arms to the core monosaccharides of the antibody peptide at the glycosylation site. More details can be found at, for example, Varki A et al, Essentials of glycobiology, Cold Spring Harbor, N.Y.: Cold Spring Harbor Laboratory Press; 1999, Chapter 7.

In some embodiments, the antibodies or fragments thereof in the present disclosure comprise a predominant portion of glycoforms containing N-linked Mannose-5 glycans. "A predominant portion" as used herein refers to a portion that is above 70%, above 80%, above 90%, above 95%, above 96%, above 97%, above 98%, above 99%, or 100% of the whole population of glycosylated antibodies containing N-linked glycoforms. The amount of glycoform contained on the antibodies or fragments thereof may be measured by a conventional detection method known in the art, for example, HPAEC-PAD.

In some embodiments, the antibody is Metuzumab or a fragment thereof. Metuzumab is an antibody whose heavy chain amino acid sequence is SEQ ID NO: 4 and light chain amino acid sequence is SEQ ID NO: 3, and which further comprises one or more glycoform(s) lacking both fucose residues and xylose residues. In some embodiments, Metuzumab contains N-linked Mannose-5 glycans.

Figure 6:
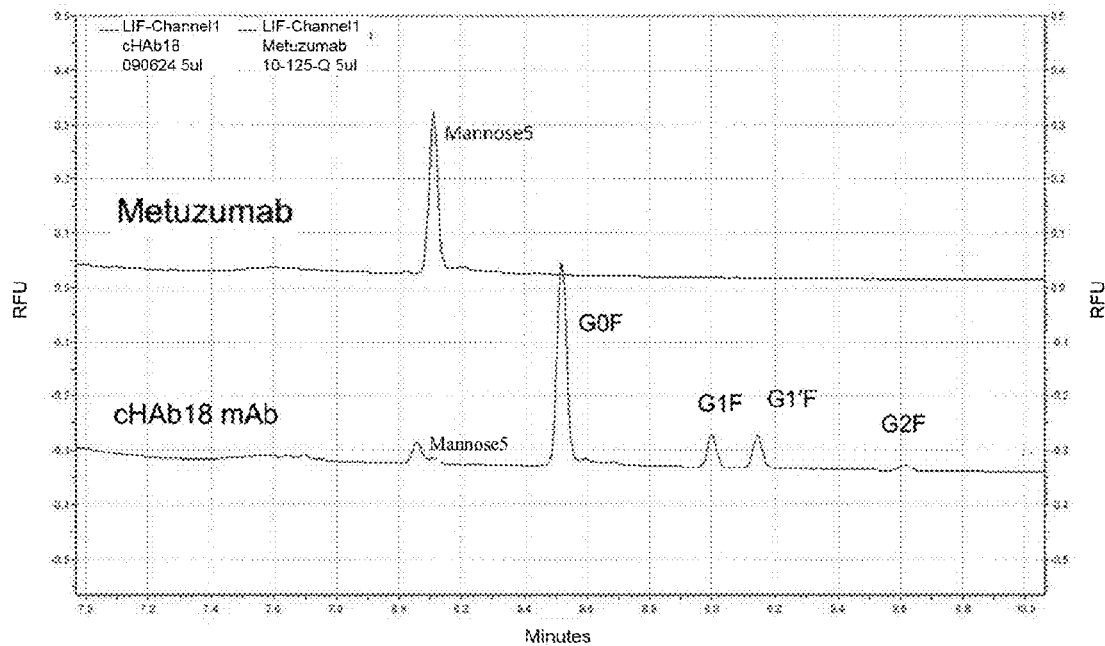
FIG. 6 shows the oligosaccharide and monosaccharide profiles of Metuzumab and cHAb18.

A glycosylation profile of Metuzumab is shown in FIG. 6. In some embodiments, the antibodies or fragments thereof provided herein have a glycosylation profile as analyzed by HPAEC-PAD that is substantially equivalent to that of Metuzumab as shown in FIG. 6. "Substantially equivalent" as used herein with respect to glycosylation profile is intended to mean the glycosylation profile is in general consistency to that shown in FIG. 6. For example, the glycosylation profile has the same number of peak(s), similar peak shape, and/or similar peak position.

In some embodiments, the antibody is obtained from an acetyl-glucosamine transferase deficient cell line. In some embodiments, the cell line is acetyl-glucosamine transferase deficient CHO cell line.

In some embodiments, the heavy chain and light chain of Metuzumab are encoded by a nucleic acid of SEQ ID NO: 8 and a nucleic acid of SEQ ID NO: 7, respectively. Metuzumab has a heavy chain and/or a light chain encoded by nucleic acids containing altered genetic codon usage based on the codon usage bias in CHO cells to increase the expression level of the heavy chain and/or the light chain in the host cell. For example, the nucleic acid encoding the light chain variant region of Metuzumab comprises an altered codon for Serine (Ser, S) which is AGC, and the nucleic acid encoding the heavy chain variant region comprises an altered codon for Leucine (Leu, L) which is CTG, and an altered codon for Lysine (Lys, L) which is AAG. In some embodiments, the host cell for production of Metuzumab is acetyl-glucosamine transferase deficient CHO-K1 MAGE 1.5 cell (obtained from Eureka therapeutics, U.S. Pat. Nos. 8,025,879, 8,080,415, 8,084,222, PCT/US2009/051325, CN200980145664.4). Although the amino acid sequences of Metuzumab are identical to those of cHAb18, the glycosylation profile of Metuzumab is different from that of cHAb18. In some embodiments, the glycosylation profile of Metuzumab exhibits homogeneous glycoform and comprises solely Mannose-5 N-linked oligosaccharide and lacks fucose and xylose.

Pharmaceutical Composition

The present disclosure further provides pharmaceutical compositions comprising an antibody that binds to an extracellular region of human CD147, or a fragment thereof, and a pharmaceutically acceptable vehicle or excipient, wherein the antibody comprises a heavy chain having the amino acid sequence of SEQ ID NO: 4 and a light chain having the amino acid sequence of SEQ ID NO: 3, and the antibody contains a glycoform lacking both fucose residues and xylose residues.

In some embodiments, the pharmaceutical compositions comprise an antibody comprising a heavy chain having the amino acid sequence of SEQ ID NO: 4, or a fragment thereof, and a pharmaceutically acceptable vehicle or excipient. In some embodiments, the pharmaceutical composition comprises an antibody comprising a light chain having the amino acid sequence of SEQ ID NO: 3, or a fragment thereof, and a pharmaceutically acceptable vehicle or excipient. In some embodiments, the pharmaceutical composition comprise an antibody comprising a heavy chain having the amino acid sequence of SEQ ID NO: 4 and a light chain having the amino acid sequence of SEQ ID NO:3, or a fragment thereof, and a pharmaceutically acceptable vehicle or excipient.

As used herein, the phrase "pharmaceutically acceptable" means that compounds, materials, compositions, and/or dosage forms are, within the scope of sound medical judgment, suitable for use in vivo in human beings and animals without excessive toxicity, irritation, allergic response, or other problem or complication, commensurate with a reasonable benefit/risk ratio. In some embodiments, compounds, materials, compositions, and/or dosage forms that are pharmaceutically acceptable refer to those approved by a regulatory agency (such as U.S. Food and Drug Administration, China Food and Drug Administration or European Medicines Agency) or listed in generally recognized pharmacopoeia (such as U.S. Pharmacopoeia, China Pharmacopoeia or European Pharmacopoeia) for use in animals, and more particularly in humans.

As used herein, the term "vehicle or excipient" refers to any and all carriers, fillers, solvents, coatings, antibacterial and antifungal agents, flavoring agents, isotonic and absorption delaying agents, and the like that are pharmaceutically acceptable and can facilitate storage and administration of the compounds of the present application to a subject. Pharmaceutically acceptable vehicle or excipient that can be employed in present disclosure includes those generally known in the art, such as those described in "Remington Pharmaceutical Sciences" Mack Pub. Co., New Jersey (1991), which is incorporated herein by reference.

In some embodiments, the pharmaceutical composition of the present disclosure further comprises one or more chemotherapeutic agents. In some embodiments, the chemotherapeutic agent is selected from gemcitabine, cisplatin, paclitaxel, navelbine, or a combination thereof. In some embodiments, the chemotherapeutic agent is gemcitabine and cisplatin.

Method for Producing an Antibody

In another aspect, the present disclosure provides methods for producing an antibody that binds to an extracellular region of human CD147, or a fragment thereof, comprising: culturing a host cell comprising a vector comprising a first nucleotide sequence encoding a heavy chain having the amino acid sequence of SEQ ID NO: 4 and a second nucleotide sequence encoding a light chain having the amino acid sequence of SEQ ID NO: 3 under a condition to allow expression of the antibody comprising the heavy chain and the light chain or a fragment thereof and obtaining the antibody or the fragment thereof from the culture.

In yet another aspect, the present disclosure provides methods for producing an antibody that binds to an extracellular region of human CD147, or fragment thereof, comprising: obtaining nucleotide sequence encoding a heavy chain having the amino acid sequence of SEQ ID NO: 4 and nucleotide sequence encoding a light chain having the amino acid sequence of SEQ ID NO: 3; constructing an vector comprising the nucleotide sequence or a fragment of the nucleotide sequence; transfecting the vector into acetyl-glucosamine transferase deficient cell line; culturing the transfected cell line in media; and obtaining the antibody or the fragment of the antibody from the culture.

In some embodiments, the step of obtaining the nucleotide sequence comprises altering the nucleotide sequence to accommodate codon usage bias to host acetyl-glucosamine transferase deficient cell line.

The step of transfecting the vector into the acetyl-glucosamine transferase deficient cell line can be performed via any method known in the art, including but are not limited to, electro-transfection, liposome transfection, viral transfection.

The culture media used in present disclosure may be any culture media suitable for culturing the host cell line, including but are not limited to, RPMI 1640, DMEM, CDM4 CHO (Hyclone), CD CHO Opti (Gibco), CHO Efficient Feed A or B (Gibco). In some embodiments, the culture media is serum free media. In some embodiments, the culture media is animal component free media. In some embodiments, the culture media is CD CHO Opti (Gibco).

In some embodiments, the step of culturing the transfected cell line in media includes a fed-batch process. In some embodiments, the step of culturing the transfected cell line in media comprises culturing the transfected cell line at 36-38° C. for a first period and then at 30-32° C. for a second period. In some embodiments, the first period is 4-10 days. In some embodiments, the second period is 11-21 days.

In some embodiments, the expression level of the antibody in the cell line is at least 100 mg/L, at least 200 mg/L, or at least 300 mg/L. In some embodiments, the expression level of the antibody in the cell line increases by at least 20 times, or at least 50 times, or at least 100 times. In some embodiments, the percentage of non-glycosylated heavy chain calculated based on the total amount of the antibody obtained is less than 10%, 7%, 5% or 3%.

Method for Treating Human CD147 Expression-related Diseases

In another aspect, the present disclosure provides methods for treating human CD147 expression-related diseases in a subject in need thereof, comprising administering an effective amount of an antibody that binds to an extracellular region of human CD147, or a fragment thereof, wherein the antibody comprises a heavy chain having the amino acid sequence of SEQ ID NO: 4 and a light chain having the amino acid sequence of SEQ ID NO: 3, and the antibody contains a glycoform lacking both fucose residues and xylose residues. In some embodiments, the methods further comprise administering a chemotherapeutic agent to the subject. In some embodiments, the chemotherapeutic agent is selected from gemcitabine, cisplatin, paclitaxel, and navelbine. In some embodiments, the disease is cancer. In some embodiments, the cancer is lung cancer, liver cancer, esophagus cancer, ovarian cancer, stomach cancer, breast cancer, cervical cancer, or colon cancer. In some embodiments, the disease is lung cancer. In some embodiments, the disease is non-small cell lung cancer.

Unless defined otherwise, all technical and scientific terms used herein have the same meaning as commonly understood by one of ordinary skill in the art to which this invention belongs.

As used herein, the singular forms "a", "an" and "the" are intended to include the plural forms as well, unless the context clearly indicates otherwise. It will be further understood that the terms "comprises", "comprising", "includes", "including", "have" and/or "having" if used herein, specify the presence of stated features, steps, operations, elements and/or components, but do not preclude the presence or addition of one or more other features, steps, operations, elements, components and/or groups thereof. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "3000 mm$^2$" is intended to mean "about 3000 mm$^2$". As used herein, the term "about," when used in reference to a particular recited numerical value, means that the value may vary from the recited value by no more than 1%.

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

Although any methods and materials similar or equivalent to those described herein can be used in the practice or testing of the present disclosure, preferred methods and materials are now described.

EXAMPLES

The following examples are presented to illustrate the present disclosure. They are not intended to limiting in any manner. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Production of Chimeric Antibody against CD147

The hybridoma cell line deposited in China General Microbiological Culture Collection Center (CGMCC NO. 0426) is used to produce a mouse monoclonal antibody against human CD147, named HAb18. DNA encoding the variable region of HAb18 was cloned as described below. Then, the mouse heavy/light chain variable region sequences were ligated to sequences of the constant region of human IgG1, and then inserted into a vector for use of producing a chimeric antibody, cHAb18.

Cloning Variable Region of HAb18

(i) Extraction of Total RNA from Hybridoma Cell Culture:

Total RNA of hybridoma cell culture producing HAb18 antibody was isolated with TRIzol reagent (Invitrogen) according to manufacturer's instruction. The quality and quantity of the RNA were determined by ultraviolet spectroscopy (260/280 nm, 1.8<ratio<2.0) and 1% denaturing polyacrylamide gel electrophoresis.

(ii) Preparation of cDNA Library from the Extracted Total RNA:

First strand cDNA was synthesized by PrimeScript RT reagent Kit (from TaKaRa) according to the manufacturer's instruction.

(iii) Amplification of Variable Regions of HAb18 by PCR

The DNA encoding the variable regions of heavy chain and light chain ($V_H$ and $V_L$) of murine anti-human monoclonal antibody HAb18 were amplified by PCR with specific primers. PCR was performed with the Phusion® High-Fidelity DNA Polymerase from NEB.

Primers for cloning the variable region of the light chain are:

$V_L$-5':
(SEQ ID NO: 9)
5'-AGCATTGTGATGACCCAGACTCCCACATT-3'

$V_L$-3':
(SEQ ID NO: 10)
5'-CCGCTTGATTTCCAACTTTGTCCCCGAGCC-3'.

Primers for cloning the variable region of the heavy chain are:

$V_H$-5':
(SEQ ID NO: 11)
5'-GAAGTGAAGCTGGAGGAGTCTGGAGGAGGCT-3'

$V_H$-3':
(SEQ ID NO: 12)
5'-TGCAGAGACAGTGACCAGAGTCCCTTGGCCT-3'

The PCR reaction was carried out under the following conditions: 40 cycles of 94° C., 1 min; 55° C., 1 min; and 72° C., 1 min; for the extension at 72° C. in the final cycle, 10 min.

(iv) PCR Product Purification and Ligation into pMD18 T Vector

The PCR products (about 360 bp and about 410 bp, respectively) was separated on a 1% agarose gel, excised, purified on E.Z.N.A.™ Gel Extraction Kit (Omega bio-tek) according to manufactures' instruction and eluted in DNAse free water.

PCR Products were ligated into pMD18 T vector (TaKaRa, Otsu, Japan) according to manufactures' instruction, transformed into *E. coli* cells, screened for positive clones and sequenced.

Construction of Expression Vector for Metuzumab

To enhance the antibody productivity in CHO-K1 cells, we optimized the codon of some amino acid codon in light/heavy chain variable region to increase the expression levels of the peptides in CHO cells. In heavy chain variable region, the codon for Leu4 was changed from CTT to CTG, the codon for Lys78 was changed from AAA to AAG. In light chain variable region, the codon for Ser1 was modified from AGT to AGC, the codon for Leu103 was changed from CTG to TTG, the codon for Lys106 was changed from AAA to AAG, the codon for Arg107 was changed from CGC to CGG. Optimized nucleotide sequences of light/heavy chain variable region are shown in SEQ ID NO: 5 and SEQ ID NO: 6 respectively.

The pQD-Hyg-GSeu vector was previously constructed in-house based on a commercial vector pcDNA3.1(−) (Invitrogen). Briefly, pcDNA3.1(−) was modified to give rise to pQD vector, followed by further engineering to incorporate hygromycin gene and the GS region. Light/heavy chain variable region sequences were synthesized with the signal peptide sequence (SEQ ID NO 13) on the 5' terminal and inserted into Nhe I+Bam HI ($V_H$) and Hind III+Xba I ($V_L$) restriction site of pQD-Hyg-GSeu vector by T4-ligase (NEB, U.S.) so that the light chain variable region and heavy chain variable region were linked to human IgG1 light chain/heavy chain constant region sequences that are previously included in the vector, respectively, to form a full length light chain encoding sequence (SEQ ID NO: 7) and a full length heavy chain encoding sequence (SEQ ID NO: 8) to generate pQD-Hyg-GSeu-cHAb18 expression vector (FIG. 1). The desirable clone was obtained after transformation, PCR based identification and sequencing analysis.

Establishment of CHO Cell Line Capable of Producing Metuzumab

The pQD-Hyg-GSeu-cHAb18 expression vector were transfected in CHO K1 and CHO K1 MAGE1.5 cells (preserved in Charles River Laboratory, 510803-MCB2) by electro-transfection using Nucleofector II (from Amaxa), respectively, to generate cell line that produce cHAb18 and cell line that produce Metuzumab.

$3 \times 10^6$ CHO K1 and CHO K1 MAGE1.5 cells were respectively collected by centrifuge at 500 rpm for 10 min at room temperature, re-suspended in 100 ul Nucleofection solution V and combined with 2 μg pQD-Hyg-GSeu-cHAb18 expression vector, 2 μg pmaxGFP® Vector. Transfer cell/DNA suspension into Amaxa cuvette and electroporated by program U-023. A Nucleofector® Program G-023 was performed for electro-transfection.

The cells treated by electro-transfection were added into a CD OPTI-CHO medium (Invitrogen) in a 6-well and desired culturing vessel and incubator for 48 hour at 37° C., 8% $CO_2$. The transfected neo+ cells were selected with 500 μg/ml Hygromycin B (Invitrogen), and the gene was amplified in 2 rounds of L-Methionine Sulfoximine (MSX, 25 μM, Sigma) pressure selection. Cell line capable of producing approximately 163 mg/L of Metuzumab was obtained using ClonePix FL (Genentix Inc).

Example 2

Expression of cHAb18 and Metuzumab in Batch Culture

CHO cells expressing cHAb18 (CHO K1-cHAb18) and CHO cells expressing Metuzumab (CHO MAGE1.5-HcHAb18) were respectively thawed and cultured in serum-free medium. Initially both cell cultures were incubated at 37° C. with 5% $CO_2$. After the cell density of the Metuzumab expressing cells reached $1\times10^6$ cells/ml (around day 4), nutrient and glucose were fed to the culture at suitable intervals (for example 2 days interval). After cell growth reached stationary phase (around 7 days for the two cell lines in this example), culture of the Metuzumab expressing cells was switched to incubation at 31° C. until the end of the culturing (around 21 days). At day 21 of cultivation, both cell cultures were harvested.

The harvested cell cultures were firstly filtrated through depth filter to remove cells. Then affinity chromatography was carried out using Mabselect Sure to capture the antibody. Finally, hydrophobic chromatography was carried out using Phenyl Sepharose High performance to further purify the antibodies. The final purity for both cHAb18 and Metuzumab were higher than 95%.

Figure 2:
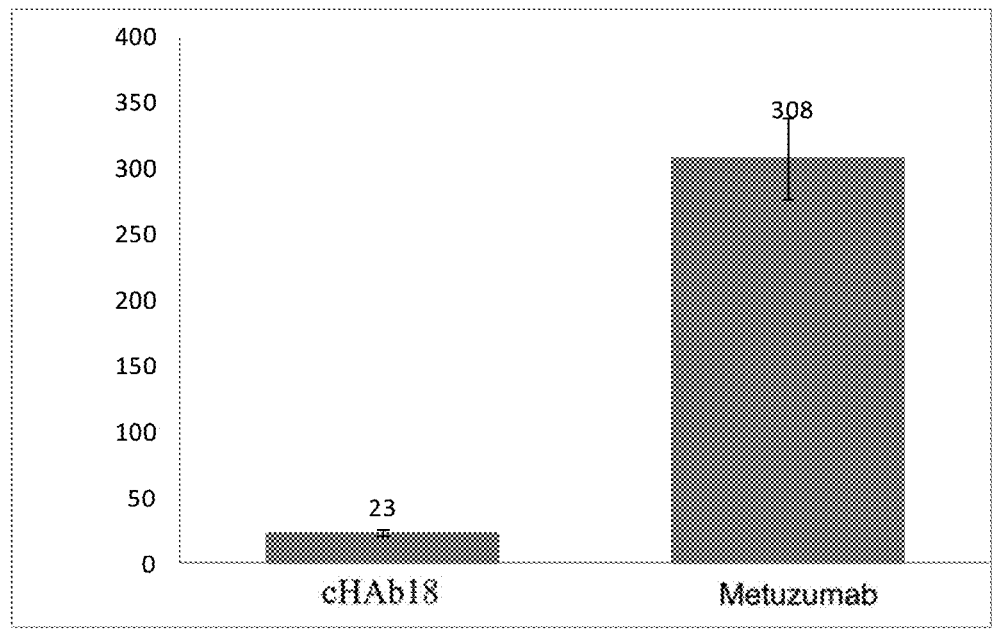
FIG. 2 shows the antibody production levels of Metuzumab in CHO MAGE1.5 cells and cHAb18 mAb produced in CHO K1 cells.

Concentrations of the antibodies were then determined by ELISA protein quantification method. Through reestablishment of the cell line (vector transfection and optimal clone selection) and adopting fed-batch and low temperature culture process, antibody concentration had been greatly improved. As shown in FIG. 2, the average mab titer of cHAb18 was 23 mg/L, the average mab titer of Metuzumab was 308 mg/L.

Example 3

Antigen-Binding Activity of Antibodies

Measurement of Antigen-Binding Activity by Surface Plasmon Resonance (SPR)

Figure 3A:
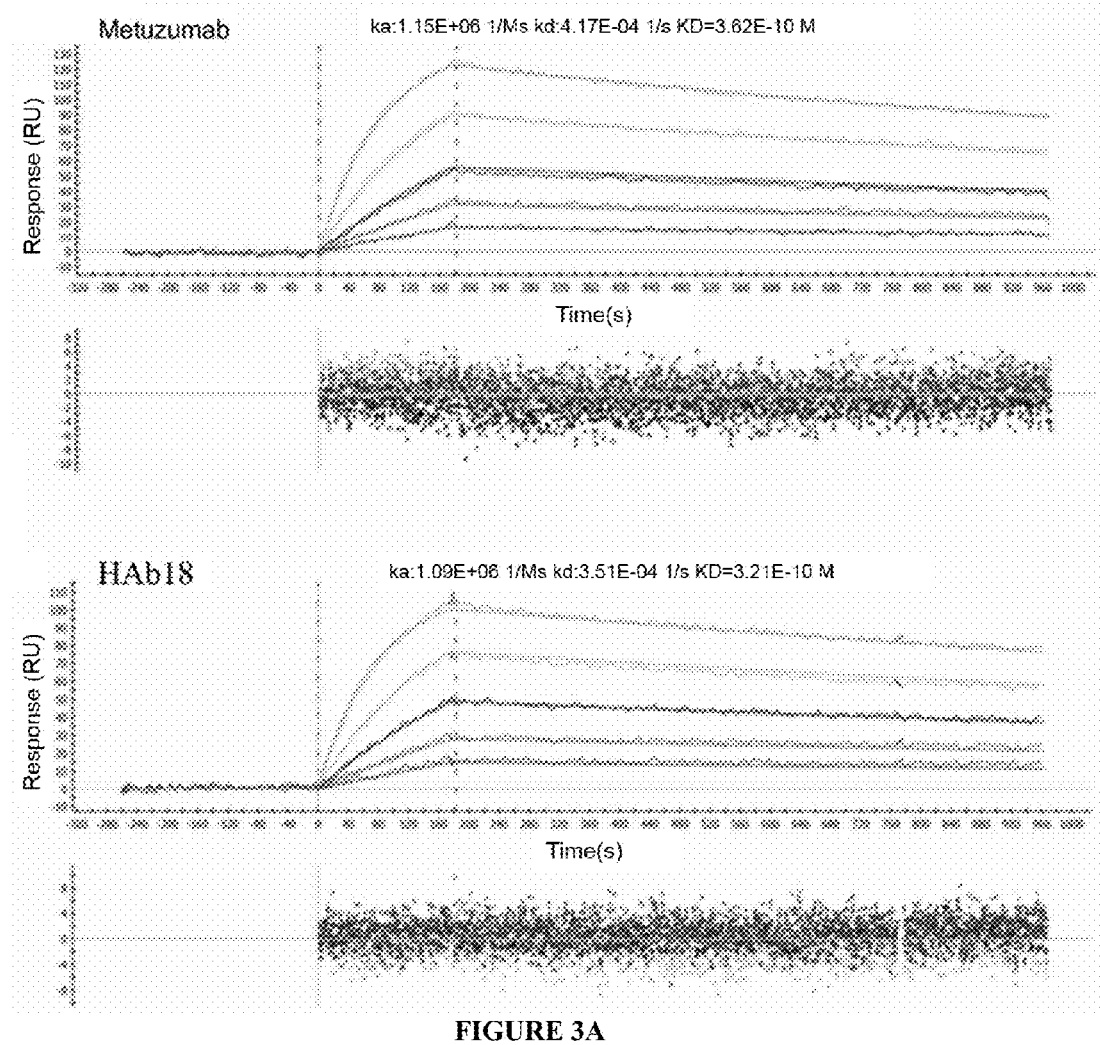
FIG. 3A shows the antigen binding kinetics of Metuzumab and cHAb18 mAb.
Figure 3B:
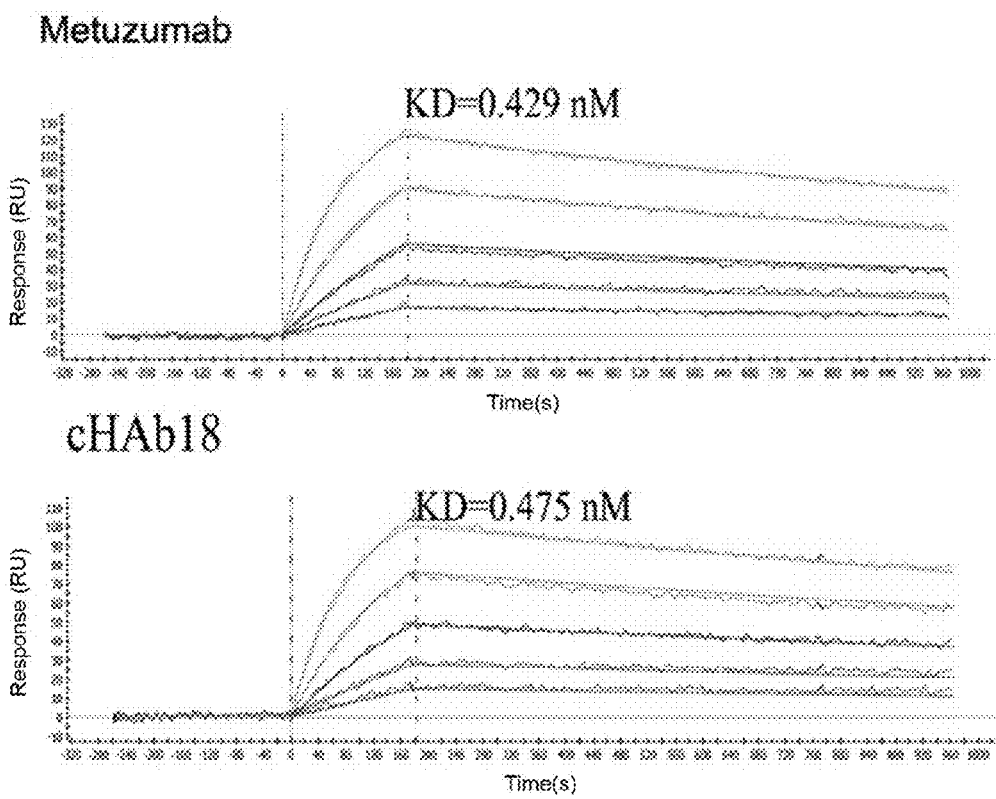
FIG. 3B shows the antigen binding kinetics of Metuzumab and cHAb18 mAb.

CD147 binding of selected antibodies (original mouse antibody HAb18, chimeric antibody cHAb18, and glycosylation modified chimeric antibody Metuzumab) were confirmed by SPR analysis (shown in FIG. 3A and FIG. 3B).

The affinity (KD) for the binding of human CD147 antigen to selected antibodies was measured by Surface plasmon resonance analysis on a multi-SPR array system (ProteOn XPR36TM, Bio-Rad). Data analysis was performed using ProteOn Manager Software (Bio-Rad). Briefly, the running buffer PBST (0.005% Tween-20 in PBS) was used continuously throughout the entire experiment at 25° C. A ProteOn GLC sensor chips (Bio-Rad) was activated for 6 min using a mixture of 0.2M EDC and 5 mM sulfo-NHS at a flow rate of 20 μl/min, followed by diluting 260 μl of 10 μg/mL each antibody in 10 mM acetate buffer at pH 4.5. The surface of the sensor chip was then deactivated with 150 μl of 1M Ethanolamine Hydrochloride (pH 8.5). The sensor surface was regenerated through a wash (about 3 min) with HBS-EP buffer until the baseline was restored. A reference cell without antibodies was prepared by a similar procedure. 5 different concentrations of human CD147 antigen (0.375, 0.75, 1.5, 3, and 6 nM) were injected in channels 1 to 5, respectively, at flow rate of 50 μl/min, 3 min. A reference channel was prepared in the same manner without injection of CD147 antigen. The SPR binding responses were collected and analyzed using the ProteOn data manager program.

Two sets of experiments were performed, in the first set of experiments, the human CD147 binding affinity of HAb18 and Metuzumab were compared (data shown in FIG. 3A), in the second set of experiments the human CD147 binding affinity of cHAb18 and Metuzumab were compared (data shown in FIG. 3B). The calculated affinities of antibodies by SPR analysis for Metuzumab and HAb18 (KD: 0.321 nmol/L and 0.362 nmol/L, respectively) can be considered equal. The calculated affinities of antibodies by SPR analysis for Metuzumab and cHAb18 (KD: 0.429 nmol/L and 0.475 nmol/L, respectively) can be considered equal. In other words, HAb18 and Metuzumab, Metuzumab and cHAb18 all exhibited similar CD147 binding ability.

Measurement of Antigen-Binding Activity by Flow Cytometry

A549 cells ($10^6$ cells) were incubated with the Metuzumab (HcHAb18) and cHAb18 antibody, respectively, in PBS with 0.1% BSA at 4° C. for 1 h. After three washes in PBS with 0.1% BSA, cells were incubated with the FITC-conjugated Rabbit anti-Human IgG Fc Secondary Antibody (Pierce) at 4° C. in the dark for 45 min. Cells were then washed three times and suspended in PBS for analysis using a FACS Calibur flow cytometer (BD, New Jersey, U.S.). Relative antigen expression is reported as median fluorescence intensity (MFI).

Figure 4:
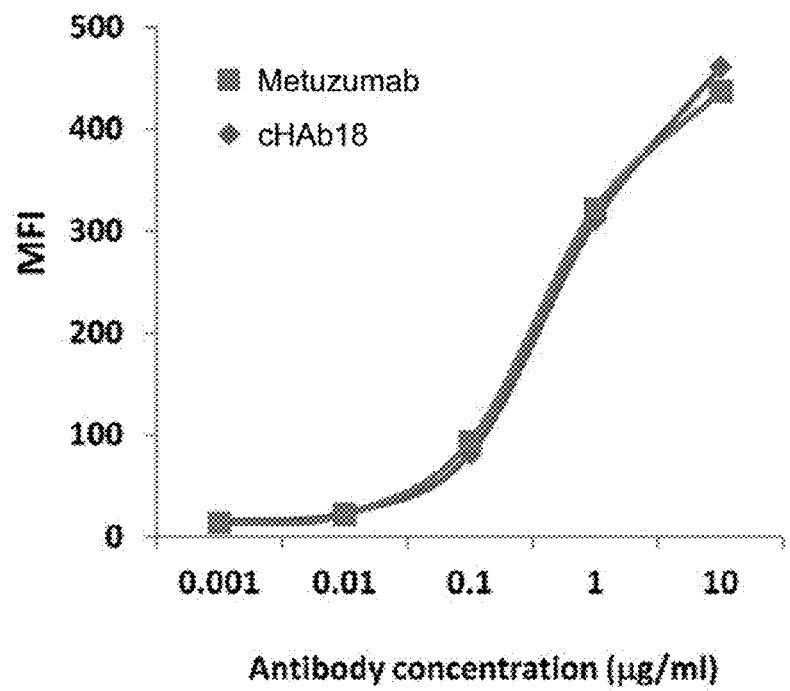
FIG. 4 shows the results of Metuzumab and cHAb18 mAbs bound to A549 cells, which are human CD147 expression cells. The antibody concentration is 0.001 µg/mL, 0.01 µg/mL, 0.1 µg/mL, 1 µg/ml and 10 µg/mL, respectively.

As shown in FIG. 4, both Metuzumab and cHAb18 bound to $CD147^+$ A549 cells, and both antibodies exhibited similar CD147-binding ability.

Example 4

Measurement of Antigen-Binding Specificity of Metuzumab

To test the specificity of Metuzumab (HcHAb18), tissue cross reactivity of Metuzumab was evaluated in FFPE tissue sections from a selected panel of human cancer tissue arrays (Chaoying Biotechnology Co., LTD, China.). Slides were microwaved for 10 min in 10 mM sodium citrated (pH 6.0), cooled for 30 min at 25° C. After incubating for 10 min in 3% $H_2O_2$ to block endogenous peroxidase, and blocking for 1 hr in 10% goat serum, slides were incubated overnight in a humidity chamber with biotinylated Metuzumab (30 μg/ml). Binding was visualized with streptavidin-conjugated peroxidase (ZsBio, China) and DAB detection system (ZsBio, China). Sections were analyzed using a bright-field microscope. The staining results were evaluated by 2 experienced pathologist in a blinded manner and classified into four categories: of 0 (no visible staining), 1+ (light brown), 2+ (mid-brown), and 3+ (dark brown), respectively, with the same intensity covering more than 75% of the staining area.

Figure 5:
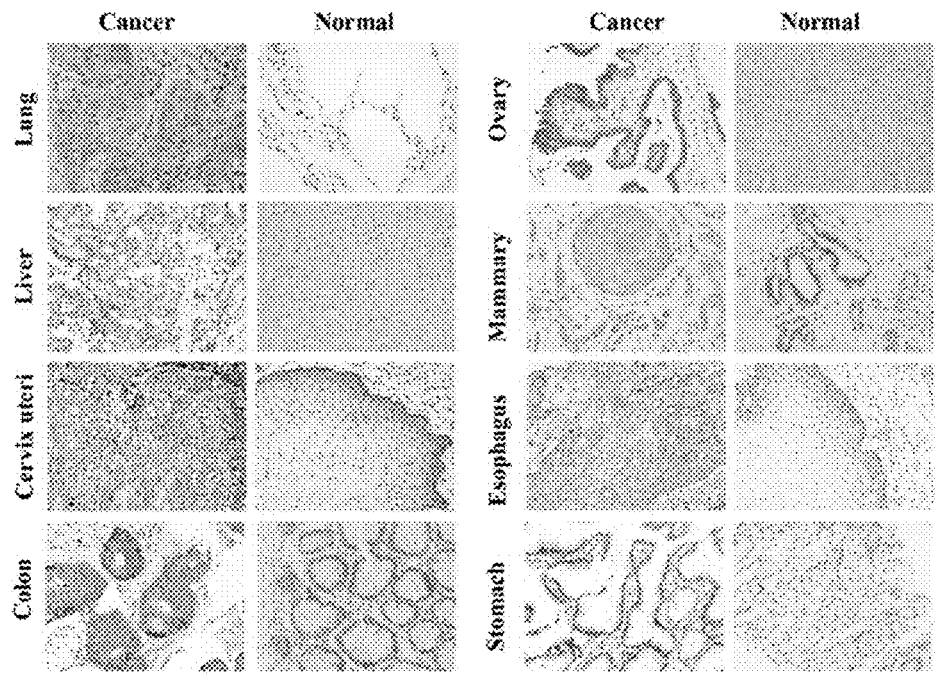
FIG. 5 shows the results of CD147-binding specificity of Metuzumab in human cancer tissue array by immunohistochemistry.

As shown in FIG. 5 and Table 1, Metuzumab specifically bound to tumor tissues, including lung cancer (60/68), ovarian cancer (9/12), stomach cancer (18/23), esophagus cancer (30/32), breast cancer (36/40), cervical cancer (17/20), liver cancer (17/20), and colon cancer (41/50). The staining pattern of the reference HAb18 was similar to that of Metuzumab in cancer tissues, suggesting that the staining detected is specific for CD147.

TABLE 1

Immuno-histo-chemical Detection of CD147 by Metuzumab in Human Cancer Arrays

| Pathology | number | 0 | 1+ | 2+ | 3+ | Positive rate | Sensitivity response rate | Specificity |
|---|---|---|---|---|---|---|---|---|
| Lung cancer | 68 | 8 | 5 | 23 | 32 | 88.24% | 88.24% | 91.67% |
| Normal lung | 12 | 10 | 2 | 0 | 0 | 8.33% | | |
| Ovary cancer | 12 | 3 | 2 | 3 | 4 | 75% | 75.00% | 100% |
| Normal ovary | 12 | 12 | 0 | 0 | 0 | 0% | | |
| gastric cancer | 23 | 5 | 1 | 7 | 10 | 78.26% | 78.26% | 80.95% |
| normal stomach | 21 | 17 | 3 | 1 | 0 | 19.05% | | |
| Esophagus cancer | 32 | 2 | 6 | 13 | 11 | 93.75% | 93.75% | 81.25% |
| Normal esophagus | 16 | 13 | 3 | 0 | 0 | 18.75% | | |
| Mammary cancer | 40 | 4 | 6 | 11 | 19 | 90.00% | 90.00% | 77.50% |
| Mammary tissue | 40 | 31 | 5 | 2 | 2 | 22.50% | | |
| cervical cancer | 20 | 3 | 2 | 5 | 10 | 85.00% | 85.00% | 100% |
| Normal cervix uteri | 4 | 4 | 0 | 0 | 0 | 0% | | |
| Liver cancer | 20 | 3 | 11 | 6 | | 85.00% | 85.00% | 75.00% |
| Normal liver | 4 | 3 | 0 | 1 | 0 | 25.00% | | |
| Colon cancer | 50 | 9 | 8 | 26 | 7 | 82.00% | 82.00% | 84.00% |
| Normal colon | 50 | 42 | 5 | 2 | 1 | 16.00% | | |

Example 5

Analysis of Oligosaccharide and Monosaccharide Profiles of Antibodies

Release of N-glycans were carried out following standard procedures (Ciucanu et al., 1984. A simple rapid method for the permethylation of carbohydrates. *Carbohydr. Res.* 131, 209 217.). Analysis of protein glycosylation was performed by using HPAEC-PAD. 60×150 mm CLC-ODS column (Shimpack, Japan) was used for the HPAEC-PAD, the column was equilibrate with washing buffer A (10 mM sodium phosphate solution (pH3.8)) at 1.0 ml/min 55° C.; then 25 µl of each testing sample were added to the column; after which washing buffer B (10 mM sodium phosphate solution (pH3.8) with 0.5% n-butyl alcohol) together with washing buffer A were used for gradient wash, within 80 min the ratio between washing buffer B and washing buffer A was linearly increased from 1:1 to 60:40; the wash-outs were tested with florescence detector with exciting light wavelength at 320 nm and emitting light wavelength at 400 nm. The oligosaccharide peaks detected were then compared with standard peaks to determine the identity of each peak.

As shown in FIG. 6, the three major peaks in the cHAb18 mAb sample correspond to masses of fucosylated oligosaccharides with G0F, G1F, G1F' glycoforms. By contrast, Metuzumab mAb exhibited homogeneous glycoform comprises solely Mannose-5 N-linked oligosaccharide, with no fucose residue or xylose residue was detected. Data demonstrated accumulation of non-fucosylated in the optimized antibody from Metuzumab instead of fucosylated structures in the native chimeric cHAb18 antibody.

Example 6

Non-Glycosylated Heavy Chain in Metuzumab

The Non-glycosylation heavy chain (NGHC) analysis methods were based on that described in the Beckman Coulter IgG Purity/Heterogeneity kit. Unless noted otherwise, a bare fused silica capillary 50 mm id with an effective length of 20.2 cm and total length of 30.2 cm was used for reduced analysis. Prior to sample injection and separation, the capillary was rinsed with basic wash for 3 min at 70 psi, acidic wash for 1 min at 70 psi, water wash for 1 min at 70 psi, and gel buffer wash for 10 min at 70 psi. Following the rinses, the capillary and electrode ends were dipped twice in separate water vials prior to sample injection at 5 kV. Another water dip was performed followed by separation at 15 kV. During separation, pressure was applied to both ends of the capillary at 20 psi. Detection was performed at 220 nm using a Pulse Distribution Analysis (PDA) detector. The percentage of NGHC in Metuzumab was measured and calculated in several independent experiments, and the percentages obtained were all below 5%.

Example 7

Antibody-Dependent Cellular Cytotoxicity (ADCC) of Metuzumab

The ADCC activity was determined by measuring lactate dehydrogenase (LDH) activity in the medium using a Cytotoxicity Detection Kit (LDH; Roche) according to the manufacturer's protocols.

In vitro ADCC assays were performed with human lung cancer cell lines (NCI-H520, A549 and NCI-H446) as target cells, and human spleen cells were used as effector cells. The target cells ($1 \times 10^4$ per well) were washed with PBS and pre-incubated with antibodies solution for 30 min at 37° C. in serum-free RPMI-1640 supplemented with 0.1% BSA. The antibody solution (Metuzumab or the chimeric antibody cHAb18 mAb) that has been adjusted to a concentration of 0.001, 0.01, 0.1, 1 or 10 µg/ml was dispensed at 100 µl/well into each well that contained the target cells, Subsequently, 100 µl of the effector cells at an effector/target ratio of 50:1 was dispensed into each well, and incubated at in a carbon dioxide incubator. The cells were incubated for an additional 24 h prior to the detection of cell death by measuring lactate dehydrogenase (LDH) activity in the medium using a Cytotoxicity Detection Kit (LDH; Roche) according to the manufacturer's protocols. The ADCC-inducing activity was calculated to the following formula: Cytotoxicity (expressed as a percentage)=(experimental cell lysis−spontaneous effector lysis−spontaneous target lysis)/(maximum target lysis−spontaneous target lysis)×100%. All assays were performed in triplicate.

Figure 7:
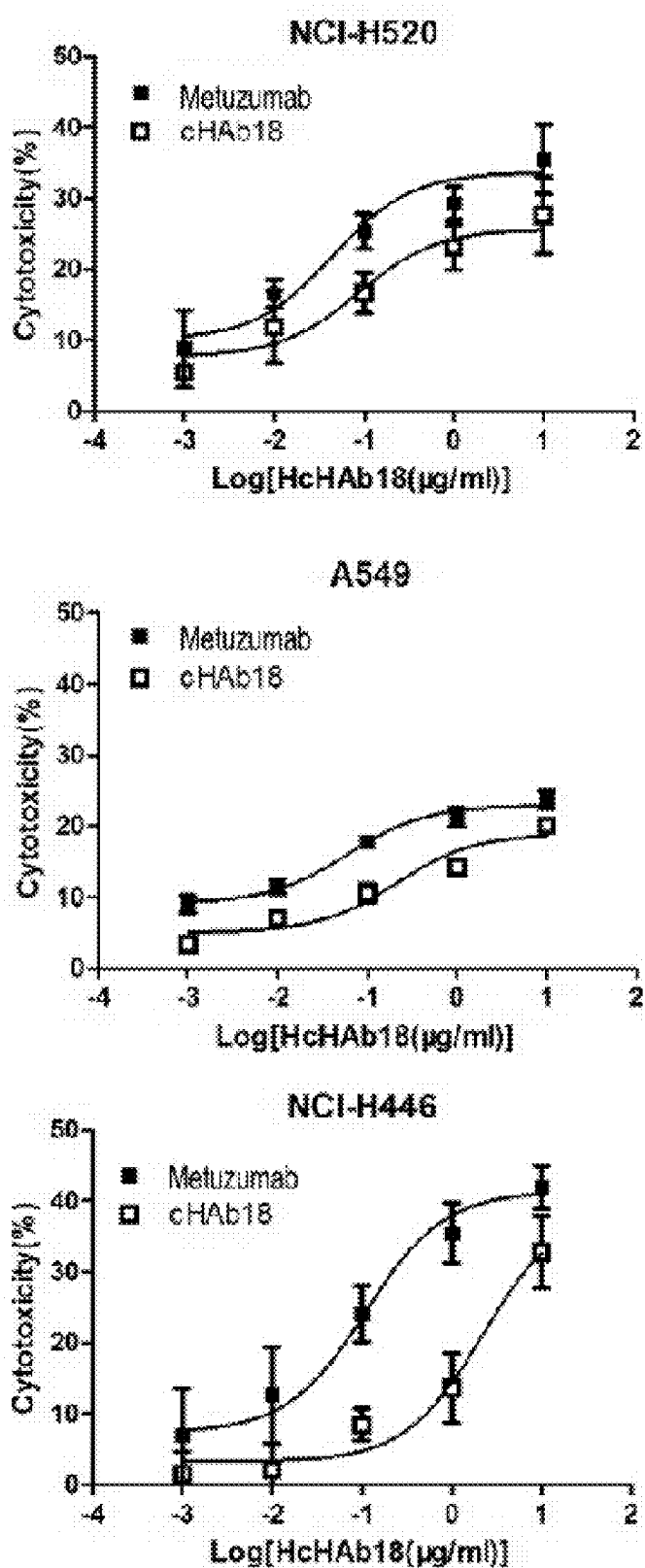
FIG. 7 shows an ADCC activity of Metuzumab on non-small cell lung cancer cells. NCI-H520, A549 and NCI-H446 cells ($1 \times 10^4$ per well) were incubated with Metuzumab or cHAb18 mAb for 30 min at 37° C. Effector cells (Spleen cells) were added at the ratio of effector cells to T cells (E/T) 50:1 for 24 hours at 37° C. in $CO_2$ incubator. After centrifugation, supernatants were harvested and lactate dehydrogenase (LDH) activity were measured. Data represent mean±SD of five independent experiments.

As shown in FIG. 7, the ADCC-inducing activity of the Metuzumab increased by about 10-folds more than that of cHAb18 mAb in all three cell line, EC50% of Metuzumab was 0.04 µg/ml, 0.06 µg/ml and 0.11 µg/ml in NCI-H520, A549 and NCI-H446 cells, respectively. No ADCC activity was found with the control antibody IgG1.

Example 8

Inhibition of Cancer Cell Invasion and Metastasis by Metuzumab

Wound healing and transwell invasion assays were performed. For wound healing assay, $2\times10^4$ cells were plated in 24-well plate to form cell monolayer and allowed to reach confluence for 2 days. A wound was made in the monolayer (at time 0) by a 200 µl tip. After wash of the monolayer, Metuzumab solution was dispensed at 0.1 µg/ml, 1 µg/ml and 10 µg/ml, respectively, at 200 µl/well into each well. Saline was used as control. The distance between two sides of an open wound was measured under a CX71 microscope (Olympus). The distance between the two sides of the wound after 20-72 h of migration was divided by the distance at time 0 and represented on a graph. The experiments were performed in triplicates, the results were shown as mean±SD.

For invasion assay, NCI-H520 or A549 cells were serum-starved for 12 hours in DMEM containing 0.1% FBS. Serum-starved cells were trypsinized and re-suspended in DMEM containing 0.1% FBS and Metuzumab solution at 0.1 µg/ml, 1 µg/ml and 10 µg/ml, respectively. $5\times10^4$ cells were added to the upper chamber of each well (6.5 mm in diameter, 8-µm pore size; Corning, N.Y.) coated with 30 mg/cm$^2$ Matrigel (BD Bioscience). Medium containing 10% FBS was placed in the lower compartment of the chamber. After 24 hours at 37° C., cells on the upper membrane surface were removed by careful wiping with a cotton swab, and the filters were fixed by treatment with 95% ethanol for 30 minutes and stained with 0.2% crystal violet solution for 30 minutes. Invasive cells adhering to the undersurface of the filter were then counted (five high-power fields/chamber) using a CX71 microscope (Olympus).

Figure 8A:
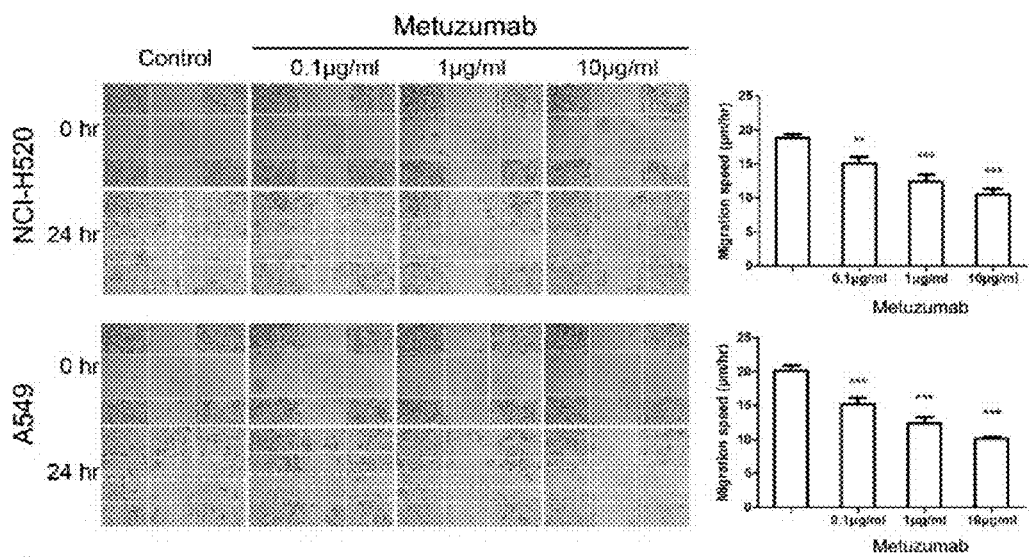
FIG. 8A shows inhibition of cancer migration by Metuzumab.

As shown in FIG. 8A, in the experiment with NCI-H520 cells, the migration rate of saline group was 18.8 µm/hr, however, the rate was 15.0 µm/hr, 12.4 µm/hr and 10.5 µm/hr in 0.1 µg/ml, 1 µg/ml and 10 µg/ml Metuzumab group, respectively. The migration activity decreased by 20.2% (P<0.01), 34.0% (P<0.001) and 44.1% (P<0.001) compared to the control group, respectively. All these data indicated that Metuzumab inhibits cell migration of NCI-H520 cells. In the experiments with A549 cells, the migration rate of control group was 20.1 µm/hr, however, the rate was 15.2 µm/hr, 12.4 µm/hr and 10.1 µm/hr in 0.1 µg/ml, 1 µg/ml and 10 µg/ml Metuzumab group, respectively. The migration activity repressed by 24.4% (P<0.05), 38.3% (P<0.001) and 50% (P<0.001) compared to the control group, respectively. The data in FIG. 8A indicated that Metuzumab inhibits cell migration of A549 cells.

Figure 8B:
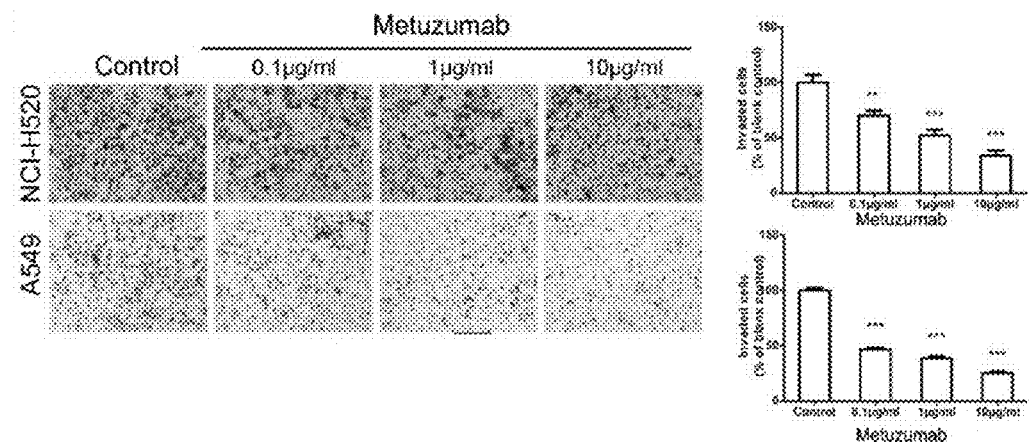
FIG. 8B shows inhibition of cancer invasion by Metuzumab.

As shown in FIG. 8B, compared to control groups, the invasiveness of NCI-H520 cells repressed by 30.0% (P<0.01), 48.0% (P<0.001) and 66.2% (P<0.001) after being treated by 0.1 µg/ml, 1 µg/ml and 10 µg/ml Metuzumab, respectively. The invasiveness of A549 repressed by 53.5% (P<0.01), 61.5% (P<0.001) and 74.6% (P<0.001) after being treated by 0.1 µg/ml, 1 µg/ml and 10 µg/ml Metuzumab compared to control groups, respectively. The data in FIG. 8B indicated that Metuzumab inhibits cell invasion of NCI-H520 and A549 cells.

Example 9

Antitumor Effects of Metuzumab in Xenograft Models

The antitumor effects of Metuzumab were confirmed using a human lung cancer-derived cell line A549 xenograft models.

Animals were housed in specific pathogen-free (SPF) condition. For the localized subcutaneous xenograft mouse model, $1\times10^6$ NCI-H520 or A549 cells, suspended in Hank's balanced salt solution were implanted in the right dorsal flank of male SCID mice (6-8 week old). When tumors reached a mean volume of 100 mm$^3$, mice were randomized into treatment cohorts (n=10 mice per group). Mice were grouped for different treatments, including Metuzumab treatment groups treated with 2 mg/kg, 10 mg/kg and 30 mg/kg Metuzumab; chemistry treatment group treated with 2 mg/kg Cisplatin and 100 mg/kg Gemcitabine; combination treatment group treated with 10 mg/kg Metuzumab with 2 mg/kg Cisplatin and 100 mg/kg Gemcitabine, or saline (control group) via tail vein, respectively. Antibody injections were administered twice weekly, for 3 weeks consecutively; chemotherapeutic agents were administered once a week, for 3 weeks consecutively. Tumor size was measured twice each week for the duration of the study using calipers. Tumor volumes were determined using the following formula: (length×width)/2. Antitumor activity was assessed by calculating inhibition ratio of tumor volumes (IRTV) based on medians by using following formula: [1−average (Ttreatment (day x)−Ttreatment (day 0))/average (Tcontrol (day x)−Tcontrol (day 0))]×100%.

Figure 9A:
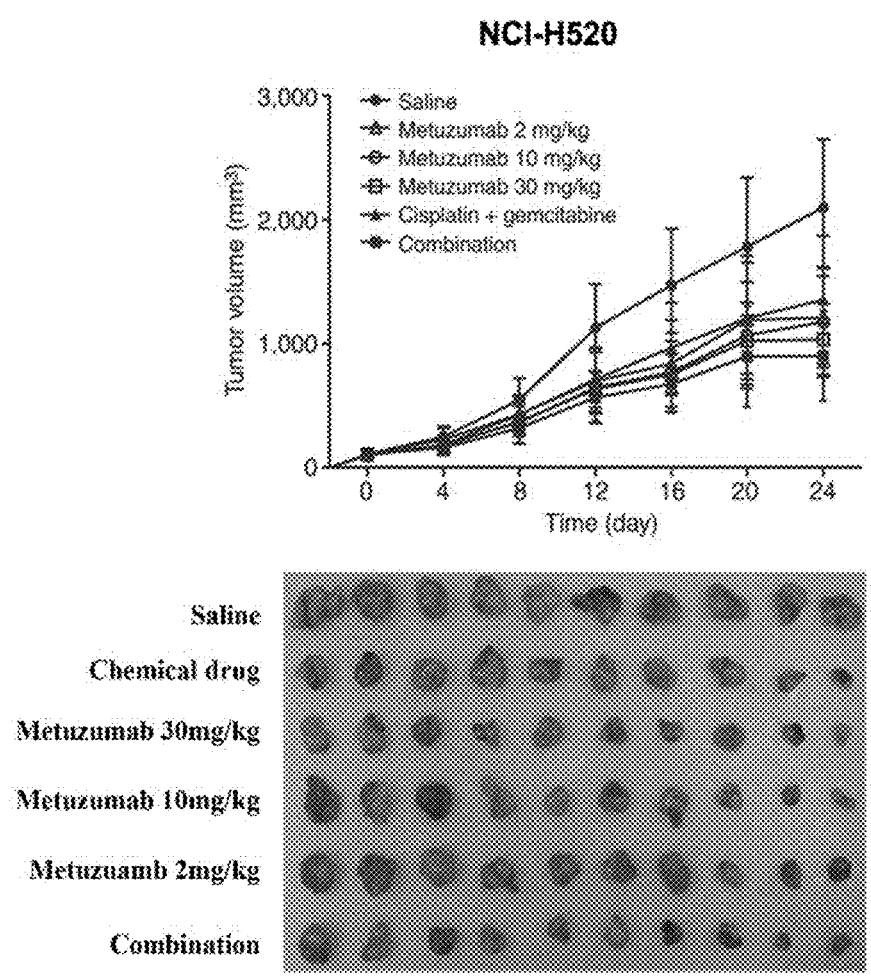
FIG. 9A shows inhibition of tumor growth in vivo by the Metuzumab. Mice injected with NCI-H520 cells subcutaneously in the right dorsal flank were treated by intravenous saline; 2 mg/kg Cisplatin and 100 mg/kg Gemcitabine; Metuzumab infusion at 2 mg/kg, 10 mg/kg and 30 mg/kg; combination of 10 mg/kg Metuzumab with 2 mg/kg Cisplatin and 100 mg/kg Gemcitabine; wherein the antibodies were injected twice weekly for 3 week consecutively, while the chemotherapeutic agents were injected once a week for 3 weeks consecutively. The tumors were measured twice a week.
Figure 9B:
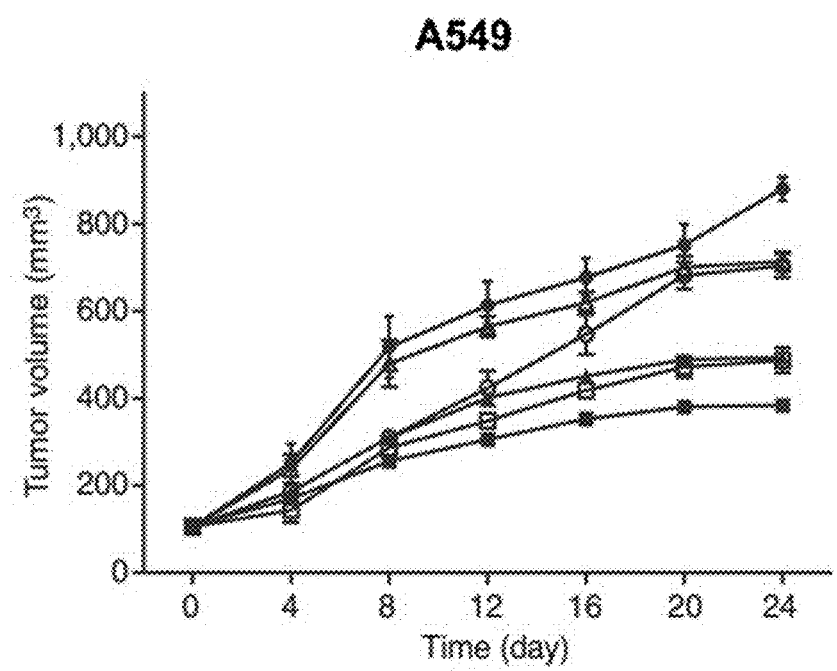
FIG. 9B shows inhibition of tumor growth in vivo by the Metuzumab. Mice injected with A549 cells subcutaneously in the right dorsal flank were treated by intravenous saline; 2 mg/kg Cisplatin and 100 mg/kg Gemcitabine; Metuzumab infusion at 2 mg/kg, 10 mg/kg and 30 mg/kg; combination of 10 mg/kg Metuzumab with 2 mg/kg Cisplatin and 100 mg/kg Gemcitabine; wherein the antibodies were injected twice weekly for 3 week consecutively, while the chemotherapeutic agents were injected once a week for 3 weeks consecutively. The tumors were measured twice a week.
Figure 9B:
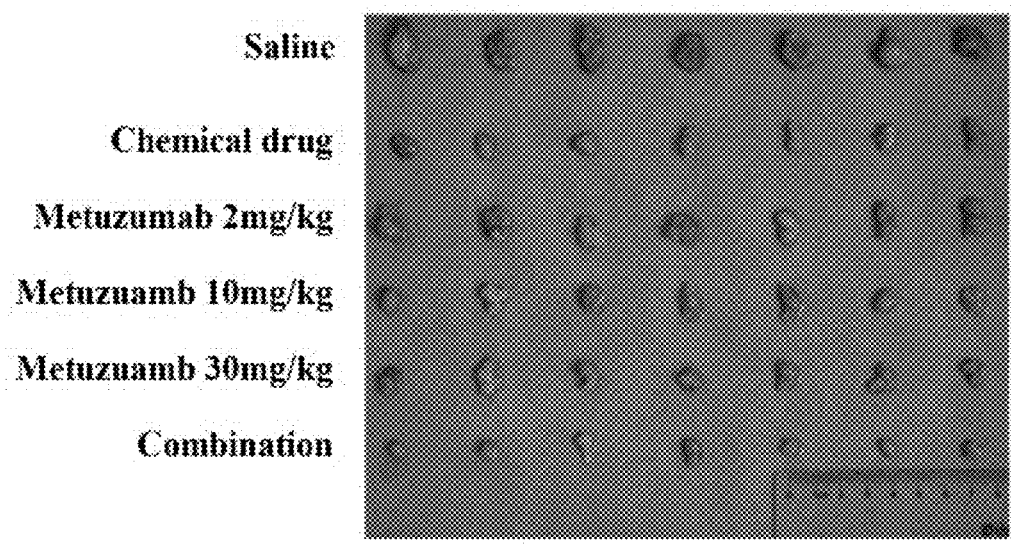

The results are shown in FIGS. 9A and 9B. All of treatment groups displayed significantly inhibition of tumor growth compared with the control treatment group (P<0.01). In the NCI-H520 models, the injection of 2-30 mg/kg Metuzumab resulted in a significant inhibition in the IR$_{TV}$ (48.85%, 49.53%, 53.34%, 57.75% for chemotherapeutic agents group, the 2 mg/kg, 10 mg/kg, and 30 mg/kg Metuzumab groups, respectively; P<0.001). In A549 models, the tumor volume inhibition rates were 14.78%, 26.52%, and 50.64% in 2, 10, and 30 mg/kg Metuzumab, respectively, (P<0.01). As a result, the Metuzumab was found to exhibit antitumor effects in all of the administration groups. As shown in the result, the combination treatment group shows better tumor growth inhibition effect than any other groups. The results indicated that the combination of Metuzumab with chemical drugs enhanced the antitumor efficacy when compared with the mAb treatment groups or chemotherapeutic agents treatment group in preclinical models of human NSCLC. Therefore, in the combination therapy the dose of the chemotherapeutics could be decreased while decreasing the side effects of chemotherapeutics and increasing the therapeutic effect.

While the invention has been particularly shown and described with reference to specific embodiments (some of which are preferred embodiments), it should be understood by those having skill in the art that various changes in form and detail may be made therein without departing from the spirit and scope of the present disclosure as disclosed herein.

REFERENCE

Baba, M., Inoue, M., Itoh, K., and Nishizawa, Y. (2008). Blocking CD147 induces cell death in cancer cells through impairment of glycolytic energy metabolism. Biochemical and biophysical research communications 374, 111-116.

Bian, H., Zheng, J. S., Nan, G., Li, R., Chen, C., Hu, C. X., Zhang, Y., Sun, B., Wang, X. L., Cui, S. C., et al. (2014). Randomized trial of [131I] metuximab in treatment of hepatocellular carcinoma after percutaneous radiofrequency ablation. Journal of the National Cancer Institute 106.

Chen, H., Wang, L., Beretov, J., Hao, J., Xiao, W., and Li, Y. (2010). Co-expression of CD147/EMMPRIN with monocarboxylate transporters and multiple drug resistance proteins is associated with epithelial ovarian cancer progression. Clinical & experimental metastasis 27, 557-569.

Chen, Z. N., Mi, L., Xu, J., Song, F., Zhang, Q., Zhang, Z., Xing, J. L., Bian, H. J., Jiang, J. L., Wang, X. H., et al. (2006). Targeting radioimmunotherapy of hepatocellular carcinoma with iodine (131I) metuximab injection: clinical phase I/II trials. International journal of radiation oncology, biology, physics 65, 435-444.

Jefferis, R. (2009). Recombinant antibody therapeutics: the impact of glycosylation on mechanisms of action. Trends in pharmacological sciences 30, 356-362.

Kataoka, H., DeCastro, R., Zucker, S., and Biswas, C. (1993). Tumor cell-derived collagenase-stimulatory factor increases expression of interstitial collagenase, stromelysin, and 72-kDa gelatinase. Cancer research 53, 3154-3158.

Kirk, P., Wilson, M. C., Heddle, C., Brown, M. H., Barclay, A. N., and Halestrap, A. P. (2000). CD147 is tightly associated with lactate transporters MCT1 and MCT4 and facilitates their cell surface expression. The EMBO journal 19, 3896-3904.

Li, Y., Xu, J., Chen, L., Zhong, W. D., Zhang, Z., Mi, L., Zhang, Y., Liao, C. G., Bian, H. J., Jiang, J. L., et al. (2009). HAb18G (CD147), a cancer-associated biomarker and its role in cancer detection. Histopathology 54, 677-687.

Liang, Q., Han, Q., Huang, W., Nan, G., Xu, B. Q., Jiang, J. L., and Chen, Z. N. (2014). HAb18G/CD147 regulates vinculin-mediated focal adhesion and cytoskeleton organization in cultured human hepatocellular carcinoma cells. PloS one 9, e102496.

Orazizadeh, M., and Salter, D. M. (2008). CD147 (extracellular matrix metalloproteinase inducer-emmprin) expression by human articular chondrocytes. Iranian biomedical journal 12, 153-158.

Philp, N. J., Ochrietor, J. D., Rudoy, C., Muramatsu, T., and Linser, P. J. (2003). Loss of MCT1, MCT3, and MCT4 expression in the retinal pigment epithelium and neural retina of the 5A11/basigin-null mouse. Investigative ophthalmology & visual science 44, 1305-1311.

Schneiderhan, W., Scheler, M., Holzi K. H., Marx, M., Gschwend, J. E., Bucholz, M., Gress, T. M., Seufferlein, T., Adler, G., and Oswald, F. (2009). CD147 silencing inhibits lactate transport and reduces malignant potential of pancreatic cancer cells in in vivo and in vitro models. Gut 58, 1391-1398.

Xu, J., Shen, Z. Y., Chen, X. G., Zhang, Q., Bian, H. J., Zhu, P., Xu, H. Y., Song, F., Yang, X. M., Mi, L., et al. (2007a). A randomized controlled trial of Licartin for preventing hepatoma recurrence after liver transplantation. Hepatology 45, 269-276.

Xu, J., Xu, H. Y., Zhang, Q., Song, F., Jiang, J. L., Yang, X. M., Mi, L., Wen, N., Tian, R., Wang, L., et al. (2007b). HAb18G/CD147 functions in invasion and metastasis of hepatocellular carcinoma. Molecular cancer research: MCR 5, 605-614.

Zeng, H. Z., Qu, Y. Q., Liang, A. B., Deng, A. M., Zhang, W. J., Xiu, B., Wang, H., and Wang, H. (2011). Expression of CD147 in advanced non-small cell lung cancer correlated with cisplatin-based chemotherapy resistance. Neoplasma 58, 449-454.

Zhao, S., Chen, C., Liu, S., Zeng, W., Su, J., Wu, L., Luo, Z., Zhou, S., Li, Q., Zhang, J., et al. (2013). CD147 promotes MTX resistance by immune cells through up-regulating ABCG2 expression and function. Journal of dermatological science 70, 182-189.

Zou, W., Yang, H., Hou, X., Zhang, W., Chen, B., and Xin, X. (2007) Inhibition of CD147 gene expression via RNA interference reduces tumor cell invasion, tumorigenicity and increases chemosensitivity to paclitaxel in HO-8910pm cells. Cancer letters 248, 211-218.

What is claimed is:

1. A nucleotide sequence comprising the sequence of SEQ ID NO: 7, and sequence of SEQ ID NO: 8.

2. A vector comprising the nucleotide sequence of claim 1.

3. A host cell comprising the vector of claim 2.

4. An antibody that binds to extracellular region of human CD147, wherein the antibody comprises a heavy chain having the amino acid sequence of amino acids 17-463 of SEQ ID NO: 4, and a light chain having the amino acid sequence of amino acids 17-230 of SEQ ID NO: 3, wherein the antibody contains a glycoform lacking both fucose residues and xylose residues, and the antibody comprises a predominant portion of glycoforms comprising N-linked oligosaccharides of Mannose-5.

5. The antibody of claim 4, wherein the antibody comprises solely a glycoform comprising N-linked Mannose-5.

6. The antibody of claim 4, wherein the antibody has a glycosylation profile as analyzed by High-Performance Anion Exchange Chromatography with Pulsed Amperometric Detection (HPAEC-PAD) that is substantially equivalent to that of Metuzumab as shown in FIG. 6.

7. The antibody of claim 4, wherein the antibody is obtained from acetyl-glucosamine transferase deficient cell line.

8. The antibody of claim 7, wherein the cell line is CHO cell line.

9. The antibody of claim 4, wherein the ADCC activity of the antibody is at least 2 times, 5 times, 10 times or 20 times higher than the ADCC activity of an antibody that contains a glycoform with fucose residues, xylose residues, or both.

10. A pharmaceutical composition comprising the antibody of claim 4, or fragment thereof, and a pharmaceutically acceptable vehicle or excipient.

11. The pharmaceutical composition of claim 10, further comprising chemotherapeutic agent.

12. The pharmaceutical composition of claim 11, wherein the chemotherapeutic agent is selected from gemcitabine, cisplatin, paclitaxel, and navelbine.

13. A method for producing the antibody of claim 4, or fragment thereof, comprising:
   obtaining nucleotide sequence encoding for a heavy chain having the amino acid sequence of amino acids 17-463 of SEQ ID NO: 4 and nucleotide sequence encoding for a light chain having the amino acid sequence of amino acids 17-230 of SEQ ID NO: 3;
   constructing a vector comprising the nucleotide sequences encoding for the heavy chain and the light chain;
   transfecting the vector into an acetyl-glucosamine transferase deficient cell line;
   culturing the transfected cell line in media;
   obtaining the antibody from the culture.

14. The method of claim 13, wherein culturing the transfected cell line in media comprises culturing the transfected cell line at 36-38° C. for a first period and then at 30-32° C. for a second period.

15. The method of claim 14, wherein the first period is 4-10 days.

16. The method of claim 14, wherein the second period is 11-21 days.

17. The method of claim 13, wherein the expression level of the antibody by the cell line is at least 100 mg/L, at least 200 mg/L, or at least 300 mg/L.

18. The method of claim 13, wherein the percentage of non-glycosylated heavy chain calculated based on the total amount of the antibody obtained is less than 10%, 7%, 5% or 3%.

19. The method of claim 13, wherein the cell line is acetyl-glucosamine-transferase-deficient CHO cell line.

20. A method for treating human CD147 expression-related disease in a subject in need thereof, comprising administering of an effective amount of the antibody of claim 4 to the subject and thereby treating the disease.

21. The method of claim 20, further comprising administering a chemotherapeutic agent to the subject.

22. The method of claim 20, wherein the disease is lung cancer.

* * * * *

SEQUENCE LISTING

```
<160> NUMBER OF SEQ ID NOS: 13

<210> SEQ ID NO 1
<211> LENGTH: 108
<212> TYPE: PRT
<213> ORGANISM: Mus musculus

<400> SEQUENCE: 1

Ser Ile Val Met Thr Gln Thr Pro Thr Phe Leu Val Val Ser Ala Gly
1               5                   10                  15

Asp Arg Val Thr Ile Thr Cys Lys Ala Ser Gln Ser Val Ile Asn Asp
            20                  25                  30

Val Ala Trp Tyr Gln Gln Lys Pro Gly Gln Ser Pro Lys Leu Leu Ile
        35                  40                  45

Phe Tyr Ala Ser Asn Arg Asn Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Pro Pro Phe
```

```
                    85                  90                  95
Thr Phe Gly Ser Gly Thr Lys Leu Glu Ile Lys Arg
                100                 105

<210> SEQ ID NO 2
<211> LENGTH: 111
<212> TYPE: PRT
<213> ORGANISM: Mus musculus

<400> SEQUENCE: 2

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Pro Tyr Tyr Thr Glu
    50                  55                  60

Ser Val Lys Gly Arg Phe Thr Ile Ser Arg Asp Asp Ser Lys Ser Ile
65                  70                  75                  80

Ile Tyr Leu Gln Met Asn Asn Leu Arg Ala Glu Asp Thr Gly Ile Tyr
                85                  90                  95

Tyr Cys Thr Arg Asp Ser Thr Ala Thr His Trp Gly Gln Gly Thr
                100                 105                 110

<210> SEQ ID NO 3
<211> LENGTH: 230
<212> TYPE: PRT
<213> ORGANISM: Artificial Sequence
<220> FEATURE:
<223> OTHER INFORMATION: Light chain/ Mus Musculus VL/ Homo sapiens CL

<400> SEQUENCE: 3

Met Gly Trp Ser Cys Ile Ile Leu Phe Leu Val Ala Thr Ala Thr Gly
1               5                   10                  15

Ser Ile Val Met Thr Gln Thr Pro Thr Phe Leu Val Val Ser Ala Gly
            20                  25                  30

Asp Arg Val Thr Ile Thr Cys Lys Ala Ser Gln Ser Val Ile Asn Asp
        35                  40                  45

Val Ala Trp Tyr Gln Gln Lys Pro Gly Gln Ser Pro Lys Leu Leu Ile
    50                  55                  60

Phe Tyr Ala Ser Asn Arg Asn Thr Gly Val Pro Asp Arg Phe Thr Gly
65                  70                  75                  80

Ser Gly Tyr Gly Thr Asp Phe Thr Phe Thr Ile Ser Thr Val Gln Ala
                85                  90                  95

Glu Asp Leu Ala Val Tyr Phe Cys Gln Gln Asp Tyr Ser Pro Pro Phe
                100                 105                 110

Thr Phe Gly Ser Gly Thr Lys Leu Glu Ile Lys Arg Thr Val Ala Ala
                115                 120                 125

Pro Ser Val Phe Ile Phe Pro Pro Ser Asp Glu Gln Leu Lys Ser Gly
        130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
                180                 185                 190
```

```
Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
210                 215                 220

Phe Asn Arg Gly Glu Cys
225             230

<210> SEQ ID NO 4
<211> LENGTH: 463
<212> TYPE: PRT
<213> ORGANISM: Artificial Sequence
<220> FEATURE:
<223> OTHER INFORMATION: Heavy chain/ Mus Musculus VH/ Homo sapiens CH

<400> SEQUENCE: 4

Met Gly Trp Ser Cys Ile Ile Leu Phe Leu Val Ala Thr Ala Thr Gly
1               5                   10                  15

Glu Val Lys Leu Glu Glu Ser Gly Gly Gly Leu Val Gln Pro Gly Gly
            20                  25                  30

Ser Met Lys Leu Ser Cys Val Ala Ser Gly Phe Thr Phe Ser Asp Ala
        35                  40                  45

Trp Met Asp Trp Val Arg Gln Ser Pro Glu Lys Gly Leu Glu Trp Val
    50                  55                  60

Ala Glu Ile Arg Ser Lys Ala Asn Asn His Ala Pro Tyr Tyr Thr Glu
65                  70                  75                  80

Ser Val Lys Gly Arg Phe Thr Ile Ser Arg Asp Asp Ser Lys Ser Ile
                85                  90                  95

Ile Tyr Leu Gln Met Asn Asn Leu Arg Ala Glu Asp Thr Gly Ile Tyr
            100                 105                 110

Tyr Cys Thr Arg Asp Ser Thr Ala Thr His Trp Gly Gln Gly Thr Leu
        115                 120                 125

Val Thr Val Ser Ala Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Arg Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320
```

```
Val Leu Thr Val Leu His Gln Asp Trp Leu Asn Gly Lys Glu Tyr Lys
            325                 330                 335

Cys Lys Val Ser Asn Lys Ala Leu Pro Ala Pro Ile Glu Lys Thr Ile
        340                 345                 350

Ser Lys Ala Lys Gly Gln Pro Arg Glu Pro Gln Val Tyr Thr Leu Pro
            355                 360                 365

Pro Ser Arg Asp Glu Leu Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 5
<211> LENGTH: 324
<212> TYPE: DNA
<213> ORGANISM: Mus musculus

<400> SEQUENCE: 5
agcattgtga tgacccagac tcccacattc ctggttgtat cagcaggaga cagggttacc      60
ataacctgca aggccagtca gagtgtgatt aatgatgtag cttggtacca acagaagcca     120
gggcagtctc ctaaaactgc tgatattctat gcatccaatc gcaacactgg agttcctgat    180
cgcttcactg gcagtggata tgggacggat ttcactttca ccatcagcac tgtgcaggct    240
gaagacctgg cagtttattt ctgtcagcag gattatagtc ctccattcac gttcggctcg    300
gggacaaagt tggaaatcaa gcgg                                           324

<210> SEQ ID NO 6
<211> LENGTH: 351
<212> TYPE: DNA
<213> ORGANISM: Mus musculus

<400> SEQUENCE: 6
gaagtgaagc tggaggagtc tggaggaggc ttggtgcaac tggaggatc catgaaactg       60 tcttgtgttg cctctggatt cacttttagt gacgcctgga tggactgggt ccgccagtct    120
ccagagaagg gacttgagtg ggttgctgaa attagaagca agctaataa tcatgcacca     180 tactatactg agtctgtgaa agggaggttc accatctcac gagatgattc caagagtatt    240
atctacctgc aaatgaacaa cttaagagct gaagacactg gcatttatta ctgtaccagg    300
gatagcacgc taccccactg gggccaaggg actctggtca ctgtctctgc a            351

<210> SEQ ID NO 7
<211> LENGTH: 693
<212> TYPE: DNA
<213> ORGANISM: Artificial Sequence
<220> FEATURE:
<223> OTHER INFORMATION: Light chain/ Mus Musculus VL/ Homo sapiens CL

<400> SEQUENCE: 7
atgggctggt cctgcatcat cctgttcctg gtggccaccg ccaccggcag cattgtgatg      60
```

```
acccagactc ccacattcct ggttgtatca gcaggagaca gggttaccat aacctgcaag      120
gccagtcaga gtgtgattaa tgatgtagct tggtaccaac agaagccagg gcagtctcct      180
aaactgctga tattctatgc atccaatcgc aacactggag ttcctgatcg cttcactggc      240
agtggatatg ggacggattt cactttcacc atcagcactg tgcaggctga agacctggca      300
gtttatttct gtcagcagga ttatagtcct ccattcacgt tcggctcggg gacaaagttg      360
gaaatcaagc ggaccgtggc cgcccccctcc gtgttcatct tccccccctc cgacgagcag      420
ctgaagtccg gcaccgcctc cgtggtgtgc ctgctgaaca acttctaccc ccgggaggcc      480
aaggtgcagt ggaaggtgga caacgccctg cagtccggca actcccagga gtccgtgacc      540
gagcaggact ccaaggactc cacctactcc ctgtcctcca ccctgacccct gtccaaggcc      600 gactacgaga agcacaaggt gtacgcctgc gaggtgaccc accagggcct gtcctccccc      660
gtgaccaagt ccttcaaccg gggcgagtgc tag                                   693

<210> SEQ ID NO 8
<211> LENGTH: 1392
<212> TYPE: DNA
<213> ORGANISM: Artificial Sequence
<220> FEATURE:
<223> OTHER INFORMATION: Light chain/ Mus Musculus VH/ Homo sapiens CH

<400> SEQUENCE: 8
atgggctggt cctgcatcat cctgttcctg gtggccaccg ccaccggcga agtgaagctg       60
gaggagtctg gaggaggctt ggtgcaacct ggaggatcca tgaaactgtc ttgtgttgcc      120
tctggattca cttttagtga cgcctggatg gactgggtcc gccagtctcc agagaaggga      180
cttgagtggg ttgctgaaat tagaagcaaa gctaataatc atgcaccata ctatactgag      240
tctgtgaaag ggaggttcac catctcacga gatgattcca gagtattat ctacctgcaa      300 atgaacaact taagagctga agacactggc atttattact gtaccaggga tagcacggct      360
acccactggg gccaagggac tctggtcact gtctctgcag cctccaccaa gggcccatcg      420
gtcttccccc tggcaccctc ctccaagagc acctctgggg gcacagcggc cctgggctgc      480
ctggtcaagg actacttccc cgaaccggtg acggtgtcgt ggaactcagg cgccctgacc      540
agcggcgtgc acaccttccc ggccgtccta cagtcctcag gactctactc cctcagcagc      600
gtggtgaccg tgccctccag cagcttgggc acccagacct acatctgcaa cgtgaatcac      660
aagcccagca acaccaaggt ggacaagaga gttgagccca atcttgtga caaaactcac       720 acatgcccac cgtgcccagc acctgaactc ctggggggga cgtcagtctt cctcttcccc       780
ccaaaaccca aggacaccct catgatctcc cggacccctg aggtcacatg cgtggtggtg      840
gacgtgagcc acgaagaccc tgaggtcaag ttcaactggt acgtggacgg cgtggaggtg      900
cataatgcca agacaaagcc gcgggaggag cagtacaaca gcacgtaccg tgtggtcagc      960
gtcctcaccg tcctgcacca ggactggctg aatggcaagg agtacaagtg caaggtctcc     1020
aacaaagccc tcccagcccc catcgagaaa accatctcca aagccaaagg gcagccccga     1080
gaaccacagg tgtacaccct gcccccatcc cgggatgagc tgaccaagaa ccaggtcagc     1140
ctgacctgcc tggtcaaagg cttctatccc agcgacatcg ccgtggagtg ggagagcaat     1200
gggcagccgg agaacaacta caagaccacg cctcccgtgc tggactccga cggctccttc     1260
ttcctctaca gcaagctcac cgtggacaag agcaggtggc agcaggggaa cgtcttctca     1320
tgctccgtga tgcatgaggc tctgcacaac cactacacgc agaagagcct ctccctgtct     1380
```

```
<210> SEQ ID NO 9
<211> LENGTH: 29
<212> TYPE: DNA
<213> ORGANISM: Artificial Sequence
<220> FEATURE:
<223> OTHER INFORMATION: Synthetic

<400> SEQUENCE: 9
agcattgtga tgacccagac tcccacatt                                              29

<210> SEQ ID NO 10
<211> LENGTH: 30
<212> TYPE: DNA
<213> ORGANISM: Artificial Sequence
<220> FEATURE:
<223> OTHER INFORMATION: Synthetic

<400> SEQUENCE: 10
ccgcttgatt tccaactttg tccccgagcc                                             30

<210> SEQ ID NO 11
<211> LENGTH: 31
<212> TYPE: DNA
<213> ORGANISM: Artificial Sequence
<220> FEATURE:
<223> OTHER INFORMATION: Synthetic

<400> SEQUENCE: 11
gaagtgaagc tggaggagtc tggaggaggc t                                           31

<210> SEQ ID NO 12
<211> LENGTH: 31
<212> TYPE: DNA
<213> ORGANISM: Artificial Sequence
<220> FEATURE:
<223> OTHER INFORMATION: Synthetic

<400> SEQUENCE: 12
tgcagagaca gtgaccagag tcccttggcc c                                           31

<210> SEQ ID NO 13
<211> LENGTH: 48
<212> TYPE: DNA
<213> ORGANISM: Artificial Sequence
<220> FEATURE:
<223> OTHER INFORMATION: Synthetic

<400> SEQUENCE: 13
atgggctggt cctgcatcat cctgttcctg gtggccaccg ccaccggc                         48
```